(12) United States Patent
Van Driessche et al.

(10) Patent No.: US 8,541,627 B2
(45) Date of Patent: Sep. 24, 2013

(54) HYDROFORMYLATION PROCESS INCLUDING CATALYST RECYCLE

(75) Inventors: Eddy T. A. Van Driessche, Eeklo (BE); Ronald D. Garton, Baton Rouge, LA (US); Corey W. Reed, Singapore (SG)

(73) Assignee: ExxonMobil Chemical Patents Inc., Houston, TX (US)

( * ) Notice: Subject to any disclaimer, the term of this patent is extended or adjusted under 35 U.S.C. 154(b) by 156 days.

(21) Appl. No.: 13/001,922

(22) PCT Filed: Aug. 19, 2009

(86) PCT No.: PCT/EP2009/005996
§ 371 (c)(1), (2), (4) Date: Mar. 18, 2011

(87) PCT Pub. No.: WO2010/022881
PCT Pub. Date: Mar. 4, 2010

(65) Prior Publication Data
US 2011/0160490 A1    Jun. 30, 2011

Related U.S. Application Data

(60) Provisional application No. 61/092,833, filed on Aug. 29, 2008.

(30) Foreign Application Priority Data

Oct. 14, 2008  (EP) .................... 08166547

(51) Int. Cl.
C07C 45/50  (2006.01)
C07C 29/14  (2006.01)

(52) U.S. Cl.
USPC ............................. 568/454; 568/456; 568/882

(58) Field of Classification Search
USPC .................................. 568/454, 882
See application file for complete search history.

(56) References Cited

U.S. PATENT DOCUMENTS

| | | |
|---|---|---|
| 2,547,178 A | 4/1951 | Spence |
| 2,744,921 A | 5/1956 | Mertzweiller et al. |
| 2,744,936 A | 5/1956 | Mertzweiller |
| 2,757,205 A | 7/1956 | Mertzweiller et al. |
| 2,841,617 A | 7/1958 | Mertzweiller |
| 3,188,351 A | 6/1965 | Lemke |
| 3,520,937 A | 7/1970 | Moell et al. |
| 3,929,898 A | 12/1975 | Nienburg et al. |
| 4,255,279 A | 3/1981 | Spohn et al. |
| 4,625,067 A | 11/1986 | Hanin |
| 5,327,105 A | 7/1994 | Liberman et al. |
| 5,354,908 A | 10/1994 | Nadler |
| 5,410,090 A | 4/1995 | Beadle et al. |
| 6,437,170 B1 | 8/2002 | Thil et al. |
| 6,723,884 B1 | 4/2004 | Grenacher et al. |
| 2005/0215828 A1 | 9/2005 | Garton et al. |

FOREIGN PATENT DOCUMENTS

| | | |
|---|---|---|
| EP | 0 183 546 | 6/1986 |
| EP | 0 835 234 | 4/1998 |
| FR | 1 089 983 | 3/1955 |
| GB | 702 950 | 8/1951 |
| WO | WO 93/24436 | 12/1993 |
| WO | WO2010/022880 | 3/2010 |

OTHER PUBLICATIONS

Beller, M. et al., "*Progress in Hydroformylation and Carbonylation*", Journal of Molecular Catalysis, A: Chemical, vol. 104, pp. 17-85 (1995).

Falbe, J., "*New Synthesis with Carbon Monoxide*", Springer-Verlag, pp. 158-176 (1980).

*Primary Examiner* — Sikarl Witherspoon
(74) *Attorney, Agent, or Firm* — Leandro Arechederra, III.

(57) ABSTRACT

An improved hydroformylation catalyst cycle is disclosed wherein the cobalt catalyst is recycled to the hydroformylation reaction mainly as a water soluble carbonyl salt, obtained from extraction of the acidic form of the homogeneous cobalt carbonyl catalyst from the hydroformylation product with an aqueous solution of a salt of a weaker acid. The organic product after extraction is submitted to a further demetalling step in the presence of a dilute acid and an oxidant. The water from this further demetalling step is suitable for use in the upstream extraction step. A free water phase present in the hydroformylation reaction product may be separated upstream from the extraction step and is suitable for use in the further demetalling step, such that the catalyst cycle has no waste water stream.

15 Claims, 1 Drawing Sheet

HYDROFORMYLATION PROCESS INCLUDING CATALYST RECYCLE

CROSS REFERENCE TO RELATED APPLICATIONS

This application is a 371 National Stage Application of International Application No. PCT/EP2009/005996, filed Aug. 19, 2009, which claims the benefit of U.S. Application No. 61/092,833, filed Aug. 29, 2008 and EP 08166547.3, filed Oct. 14, 2008, the disclosures of which are herein incorporated by reference in their entireties.

FIELD OF THE INVENTION

The present invention relates to hydroformylation processes, and in particular to the recovery and recycle of cobalt catalyst from carbonylation or hydroformylation reactions catalysed by homogeneous cobalt carbonyl complexes. This invention is particularly but not exclusively useful in removing dissolved cobalt from crude products formed by the homogeneous cobalt-catalysed hydroformylation of olefinic feedstocks having a carbon number in the range $C_3$ to $C_{14}$, particularly $C_5$ to $C_{12}$.

BACKGROUND OF THE INVENTION

Hydroformylation is a well known process in which an olefin is reacted with carbon monoxide and hydrogen in the presence of a catalyst to form aldehydes and/or alcohols containing one carbon atom more than the feed olefin. In high pressure hydroformylation processes, i.e. at pressures of 100 bar gauge or above, the catalyst is typically a homogeneous metal carbonyl complex, typically of a transition metal of Group VIII of the Periodic Table and carbon monoxide. Within the metals of this Group VIII, cobalt and rhodium are the best known for their hydroformylation activity, but others including palladium, iridium, ruthenium and platinum are also suitable. Cobalt is particularly preferred for the high pressure hydroformylation of olefinic feedstocks that are rich in branched and internal olefins. The cobalt carbonyl catalyst typically produces oxygenated product mixtures that are richer in the usually more desired less branched isomers, as compared to the carbonyl catalysts of the other metals, in particular of rhodium.

The present invention is concerned with the recovery and recycle of cobalt carbonyl catalyst from the hydroformylation reaction, also known as the Oxo or the oxonation reaction.

The starting liquids that are involved in high pressure hydroformylation comprise olefins which may be mixtures of olefins such as those obtained from olefin oligomerisation units. For example the olefins may be mixtures of $C_5$ to $C_{12}$ olefins obtained by the phosphoric acid or zeolite catalysed oligomerisation of mainly $C_3$ and $C_4$ olefins and mixtures thereof. $C_5$ olefins may also be present during oligomerisation, as well as traces of ethylene. Where olefin mixtures are used as feed for hydroformylation, they may have been fractionated to obtain relatively narrow boiling cut mixtures of mostly the appropriate carbon number for the production of aldehydes and alcohols with the desired carbon number. Alternatively the olefins may be obtained by other oligomerisation techniques. Such techniques include the dimerisation or trimerisation of butene using a nickel-based or nickel oxide catalyst, like the Octol® process or the process described in U.S. Pat. No. 6,437,170. Others include oligomerisation processes for ethylene, propylene, pentenes and/or butenes, preferably single carbon number feedstocks and more preferably the unbranched, even more preferably terminal olefins such as butene-1, using a nickel salt and involving di-alkyl aluminium halides, like the range of Dimersol® processes. Yet other processes employ a zeolite or a molecular sieve oligomerisation catalyst for the oligomerisation of propylene and/or butenes and/or pentenes. The olefin products of these processes are typically branched and contain relatively low amounts of linear olefin isomers, typically less than 10% wt.

The olefins may also be obtained from ethylene growth processes, such as the SHOP or the Ziegler processes, in which case they are often straight chain, preferably terminal olefins, and are called linear alpha olefins or normal alpha olefins. The SHOP process may include a metathesis step, in which case also uneven carbon numbers may be produced. The olefins from ethylene growth may have $C_6$, $C_8$, $C_{10}$ or $C_{12}$, or even higher carbon numbers such as up to $C_{14}$, $C_{16}$, $C_{18}$ or even $C_{20}$, or they can be mixtures obtained from the Fischer-Tropsch process for the conversion of synthesis gas to hydrocarbons, which generates olefins of a range of carbon numbers, primarily containing terminal olefins but which may show some side branches along their longest alkyl chain, and which may also contain some internal olefins, linear and branched. In this case, also the higher carbon numbers may be useful starting liquids. Fischer-Tropsch olefins suitable for high pressure hydroformylation are disclosed in EP 835 234, but many other disclosures in this field may readily be found. The Fischer-Tropsch process uses syngas as the starting material, and suitable sources thereof are disclosed further below in a separate paragraph.

The starting materials for the olefin oligomerisation processes mentioned above may be obtained from fluid catalytic cracking (FCC), from the steam or thermal cracking of gasses such as ethane and propane, of liquids such as liquefied petroleum gasses (LPG), of naphtha, of gasoil or heavier distillate, or even of whole crude. The oligomerisation starting material may also come from oxygenate-to-olefin processes, and from paraffin dehydrogenation processes.

The gases that are involved in high and medium pressure hydroformylation reactions include carbon monoxide and hydrogen, frequently supplied in a mixture that is known as synthesis gas or "syngas". Syngas can be obtained through the use of partial oxidation technology (POX), or steam reforming (SR), or a combination thereof that is often referred to as autothermal reforming (ATR). Thanks to the water-gas-shift reaction for supplying the hydrogen, it can be generated from almost every carbon containing source material, including methane, natural gas, ethane, petroleum condensates like propane and/or butane, naphtha or other light boiling hydrocarbon liquids, gasoline or distillate-like petroleum liquids, but also including heavier oils and byproducts from various processes including hydroformylation, and even from coal and other solid materials like biomass and waste plastics, as long as these provide a carbon source and can be brought into the reaction zone. When using liquid feeds for syngas generation, a steam reformer may involve a pre-reformer to convert part of the feed to methane or other light hydrocarbon gasses before entering the actual reformer reaction. The use of coal as feedstock for generating syngas is well known, preferably via the POX or ATR route. Such syngas may be fed directly as syngas feed for hydroformylation, but also as a feed to a Fischer-Tropsch process to generate the olefin feedstocks for the hydroformylation reaction. The latter is of interest for geographic regions where the other above-mentioned carbon sources, in particular oil and gas, are less abundant.

In the production of higher alcohols, the metal catalyst is used for the reaction of the olefins with synthesis gas. After completion of the hydroformylation (oxonation) reaction, the metal catalyst must be removed from the reaction products. For economic reasons the metal is preferably recycled for use as the catalyst in the oxonation reaction. For environmental reasons it is important that the level of metal in any waste streams from the process be minimized. More preferably, the catalyst cycle does not involve a waste stream.

The Group VIII transition metals such as cobalt are potentially hazardous and expensive materials. They may also impair downstream process steps, such as hydrogenation of the aldehyde-containing hydroformylation product to form the alcohol. Accordingly there are both environmental and economic benefits to be realized by improving the catalyst metal recovery and recycle from hydroformylation reactions.

The Group VIII transition metal species that is generally the active form of the catalyst for hydroformylation is a carbonyl compound. In the case of cobalt, it is a cobalt carbonyl and is typically hydr(id)ocobalt (tetra)carbonyl, $HCo(CO)_4$. Under reaction conditions, it is believed that the following equilibrium reaction occurs, and under high pressure and temperature conditions the equilibrium is significantly shifted to the left.

$$2HCo(CO)_4 \longleftrightarrow Co_2(CO)_8 + H_2 \qquad (1)$$

The hydroformylation catalyst is typically homogeneous, i.e. dissolved in a reaction phase, and more typically in the organic reaction phase. Hence, significant amounts of it typically remain in the product of the hydroformylation reaction, and must be removed therefrom and preferably recycled.

Several technologies for recovery and recycle of a cobalt catalyst from the hydroformylation reaction are known. The commercially more important technologies for operating an oxo catalyst cycle are described by J. Falbe in "New Synthesis with Carbon Monoxide", Springer-Verlag, 1980, in particular on pages 158 to 176. A more recent review may be found in Beller et al., "Progress in hydroformylation and carbonylation", Journal of Molecular Catalysis, A: Chemical, 104 (1995) pages 17-85.

One family of hydroformylation catalyst cycles involves the substantially complete decomposition of the cobalt carbonyl to a water soluble salt, having cobalt as the cation, and preferably with the anion of a low molecular weight organic acid, while simultaneously extracting the cobalt salt into an aqueous phase for separation from the organic hydroformylation product.

These techniques may use an oxidant, e.g. an oxygen-containing gas or air, such as those being described in U.S. Pat. Nos. 2,547,178 (Spence), 3,520,937 (Moell et al), 3,929,898 (Nienburg et al) and 6,723,884 (Grenacher et al), and are often called "air-demetalling". The technique is based primarily on the following reaction, shown here for acetic acid, during which the cobalt moves from the organic to the water phase:

$$2HCo(CO)_4 + 3/2O_2 + 4CH_3COOH \longrightarrow 2Co(CH_3COO)_2 + 3H_2O + 8CO \qquad (2)$$

The technique may alternatively use the dilute acid solution without an oxidant, such as described in GB 702 950, FR 1 089 983 or U.S. Pat. Nos. 2,744,936 and 2,841,617 (Mertzweiller), in which case it is typically called "airless demetalling". This alternative takes advantage of the following so-called "disproportionation" reaction:

$$3Co_2(CO)_8 \longleftrightarrow 2Co^{2+} + 4Co(CO)_4^- + 8CO \qquad (3)$$

Because $Co_2(CO)_8$ is practically insoluble in water, reaction (3) occurs at the oil/water interface. The equilibrium of reaction (3) is influenced by the presence of CO. Under sufficiently strong acidic reaction conditions, this may be followed by:

$$Co(CO)_4^- + H^+ \longleftrightarrow HCo(CO)_4 \qquad (4)$$

The undissociated cobalt carbonyl product from reaction (4) may then move again to the organic phase, and a reaction loop over reactions (1), (3) and (4) may be formed, which ultimately destroys all cobalt carbonyls and ends up with all cobalt as $Co^{2+}$, similar to the result of the air demetalling technique described hereinbefore, but now without the help of an oxidant.

The technique described in U.S. Pat. No. 2,744,921 uses such an airless demetalling step. The cobalt-containing water is routed to a catalyst plant where it is mixed with an olefin solution containing a sodium salt of a heavier organic acid, and air is introduced into that mixture to ensure all cobalt carbonyls are oxidised to $Co^{2+}$ before or at the same time as converting the water soluble cobalt salt to a cobalt soap of the heavier organic acid, which is then transferable to the hydroformylation reaction in an organic carrier.

In these techniques, substantially all of the cobalt carbonyl species are destroyed. In these disclosed techniques, the cobalt is oxidised from its (−1) oxidation state in $HCo(CO)_4$ and/or its (0) oxidation state in $Co_2(CO)_8$ into its $Co^{2+}$ oxidation state in the water soluble cobalt formate or acetate. Upon recycling, and it is believed also before any hydroformylation can occur, the cobalt must be reconverted to the active carbonyl form by reacting it with carbon monoxide and optionally also hydrogen in the so-called "preforming" reaction, also called metal carbonylation.

This preforming reaction may be performed in the hydroformylation reactor itself, or in an additional reactor upstream thereof, which is typically called a preformer or preforming reactor. Such preforming reactor typically operates at high temperature and high pressure, and adds significant complexity to the process. If the preforming reaction is performed in the presence of olefin feed, such as in the hydroformylation reactor itself, the preforming reaction may be impaired by components present in that feed, such as di-olefins, resulting in a delayed initiation of the hydroformylation reaction, particularly noticeable at start-up.

Many of these techniques have another drawback, i.e. that they are limited by the water solubility of the cobalt salt, which limits the amount of catalyst metal that can be made available to the hydroformylation reactor, or alternatively increases the volume of water that needs to be passed through the reactor and thereby reduces the volumetric efficiency of the high pressure reactor, which is typically an expensive equipment item. An alternative to overcome this limitation is to add an extraction step between the preformer and the hydroformylation reactor, such as described in U.S. Pat. No. 3,929,898, so that the metal carbonyl is extracted into an organic carrier for transfer to the hydroformylation reactor. This again adds significant further complexity and investment cost to the catalyst cycle.

Because of these drawbacks, catalyst cycles retaining the cobalt in the carbonyl form have been searched for and identified.

One example is the so-called "Kuhlmann cycle", described for example in U.S. Pat. No. 3,188,351 (Lemke), in which, by contact with a dilute sodium base, a sodium salt of the cobalt carbonyl is formed and separated in an aqueous solution from the hydroformylation product, the so-called "carbonylate" solution. By adding later a strong acid to this carbonylate, volatile $HCo(CO)_4$ is formed, which may be stripped at low pressure from the liquid and carried with the stripping gas to an absorber for absorption into the feed olefin. Alternatively, the acidified carbonylate is contacted with an organic, such as the feed olefin, for extraction of the undissociated HCo(CO)$_4$ and recycling with the olefin to the oxo reaction. This technique can be made highly efficient in maintaining the cobalt as carbonyl throughout the catalyst cycle, and avoids the need for large volumes of water to pass through the hydroformylation reactor. Drawbacks of this technique are the consumption of chemicals and the environmental burden related to the disposal of the dilute acid stream that is left over after the stripping step.

An alternative is the so-called "Cobalt Flash" technique, which is described in U.S. Pat. No. 4,625,067 (Hanin). In this technique, volatile HCo(CO)$_4$ is stripped directly from the organic liquid hydroformylation product and absorbed into the olefin feed for recycle to hydroformylation. Only a part of the cobalt may typically be recovered by stripping. Typically a smaller portion of the cobalt in the hydroformylation product converts to its water soluble salt of an acid that is provided, typically to cobalt formate, and upon separation and concentration of the solution thereof, and optionally a preforming step, such as proposed in WO 93/24436, this cobalt may also be recycled to hydroformylation. Several variations of this technique are known, such as in combination with an airless demetalling step as described in U.S. Pat. No. 5,410,090 (Beadle et al), or in a number of alternative combinations with an air demetalling step as described in U.S. Pat. No. 5,327,105 (Summerlin). An improved cobalt absorption step is disclosed in U.S. Pat. No. 5,354,908, offering a more concentrated cobalt containing olefin stream for feeding to the hydroformylation reaction. Again, no large volumes of water need to be passed through the hydroformylation reactor. These "Cobalt Flash" techniques provide significant environmental and operational benefits, as they may be operated with little or no byproduct waste streams. However, they are relatively complex techniques.

Intermediate alternatives are also known, in which only a part of the cobalt carbonyl is decomposed and a significant remainder of the cobalt is retained in its carbonyl form.

U.S. Pat. No. 4,255,279 (Spohn et al) describes a cobalt hydroformylation catalyst cycle wherein the cobalt is removed from the crude oxo product by dual demetalling, i.e. in two consecutive steps. In the first step, the oxo product is treated with an aqueous solution of a $Co^{2+}$ salt of an acid to form an aqueous phase containing Co[Co(CO)$_4$]$_2$, ideally with only the following neutralisation and extraction reaction taking place:

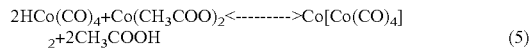
$$2HCo(CO)_4 + Co(CH_3COO)_2 \longleftrightarrow Co[Co(CO)_4]_2 + 2CH_3COOH \quad (5)$$

In a subsequent second demetalling step, the demetalling of the oxo product is completed by an air-demetalling step to form an aqueous solution of a $Co^{2+}$ salt of an acid, using reaction (2) as explained hereinbefore.

The aqueous solution from the second demetalling step is then used as the feed to the first demetalling step. The aqueous phase from the first demetalling step, containing Co[Co(CO)$_4$]$_2$, is separated and optionally treated with synthesis gas for preforming any excess $Co^{2+}$ salt that may be present to make more Co[Co(CO)$_4$]$_2$. A portion of the cobalt carbonyls are then extracted from the aqueous phase that contains the Co[Co(CO)$_4$]$_2$, at high pressure and into an organic solvent, which organic product is then passed to the oxo reactors as catalyst in an active non-aqueous form. The aqueous phase left over from the high pressure extraction and containing all the $Co^{2+}$ plus a significant portion of the cobalt carbonyls from the starting Co[Co(CO)$_4$]$_2$ is returned to the second demetalling step, where all cobalt carbonyls have to be destroyed in order to prevent them leaving with the organic reaction product. This creates a significant excess of $Co^{2+}$ presence and circulation in the catalyst cycle. The high pressure extraction step as part of the process of U.S. Pat. No. 4,255,279 avoids the risk of flooding the oxo reactors, and eliminates corrosion concerns associated with the injection of an aqueous cobalt solution directly into the oxo reactors. However, the process of U.S. Pat. No. 4,255,279 has the disadvantage that only a part of the cobalt in the aqueous phase from the first demetalling step reaches the oxo reactors and becomes available as catalyst in the hydroformylation reaction. The remaining part returns to demetalling, first to the second step for all cobalt to be converted to $Co^{2+}$, from which it is recycled to the first step in order to provide all the $Co^{2+}$ needed to participate as Co(CH$_3$COO)$_2$ in the extraction reaction (5).

The process of U.S. Pat. No. 4,255,279, in practice, leads to an excess $Co^{2+}$ being present over that needed for the Co[Co(CO)$_4$]$_2$ formation. This excess $Co^{2+}$ is formed firstly because cobalt carbonyls remain in the aqueous phase returning from the high pressure extraction step, and secondly because not all cobalt carbonyls that are present in the Oxo product are extracted in the first demetalling step. U.S. Pat. No. 4,255,279 needs an additional and complex high pressure preforming (and extraction) step in order to correct for this excess $Co^{2+}$ formation and to allow not even two thirds of the cobalt in the cobalt water recycle to the preformer to reach the oxo reactors.

Using olefins as the organic extraction liquid, as is preferred in U.S. Pat. No. 4,255,279, should make that process even more complex, because under the preforming conditions the hydroformylation reaction should also take place, and it is strongly exothermic and needs to be controlled. Performing the extraction with the olefins is at the 77° F. at which the equilibrium distribution of HCo(CO)4 is shown, makes the process even more complex by adding an extra high pressure cooler between preformer and extraction. U.S. Pat. No. 4,255,279 teaches away from recycling an aqueous stream of Co[Co(CO)$_4$]$_2$ to the oxo reactors as catalyst, as was disclosed 25 years earlier in U.S. Pat. No. 2,757,205, because of the risk of flooding the reactors.

The cobalt catalyst cycle in U.S. Pat. No. 2,757,205 (Mertzweiller et al) uses carbonyl extraction and "airless demetalling" in a single demetalling step, treating the hydroformylation product with a dilute aqueous acid in presence of synthesis gas. The resulting aqueous solution of Co[Co(CO)$_4$]$_2$ and cobalt acetate is recycled directly and entirely to the hydroformylation reaction. A concentration step is proposed on this recycle, but due to the presence of cobalt carbonyls this is not able to provide a cobalt-free water side stream. The demetalling step in U.S. Pat. No. 2,757,205 requires careful control of temperature, a definite partial pressure of synthesis gas and hence of CO, and a residence time of 30-120 minutes. These conditions represent a balancing compromise, on one hand to promote the slow interface reaction (3), which is equilibrium limited, helped by the use of high temperature but impaired by the CO partial pressure, and on the other hand to inhibit any carbonyl breakdown reactions thanks to the high CO partial pressure. The aldehyde product after treatment therefore still contains significant levels of catalyst metal, such as 54-250 ppm of cobalt. A further hot water washing step is therefore needed in U.S. Pat. No. 2,757,205 to substantially complete the decobalting of the hydroformylation reaction product. Due to the high levels of cobalt remaining after the first demetalling step, caused by the equilibrium at the process conditions, the hot water washing step only reaches a cobalt level of 8 ppm by weight, which is unacceptably high in todays operations. This washing step introduces significant amounts of water into the catalyst cycle, which has to be removed from the aqueous part of the cycle somewhere, in order to maintain a constant water inventory. The water from this washing step may be employed as the diluent for the organic acid used in the demetalling, but should first be concentrated to maintain the water balance of the system. The process in U.S. Pat. No. 2,757,205 has the advantage that all the cobalt in the recycle stream from the decobalting settler reaches the hydroformylation reaction. Because of the need for high residence times and intense mixing however, this process has the disadvantage that it requires large hold-up volumes of organic liquid in the decobalting section. This requires large equipment sizes and adds to safety concerns for operating the overall process, to a level that is unacceptable for a world scale alcohol plant of today.

There remains therefore still a need to provide a simpler, more effective and volume-efficient catalyst cycle for hydroformylation reactions. We have found that a significant improvement in volume efficiency may be achieved in the demetalling step. We have also found that, in the recycle of the metal carbonyl to the hydroformylation reaction, the need for a complex preforming and carbonyl extraction step, before and separate from the hydroformylation, may thereby also be avoided.

SUMMARY OF THE INVENTION

The invention provides for a process for hydroformylating an olefin feed in the presence of a homogeneous catalyst to form an organic hydroformylation reaction product, the catalyst comprising a carbonyl compound of a first metal which is cobalt, which process comprises:
(a) performing a first demetalling step (101) comprising contacting the organic cobalt catalyst-containing reaction product (11) with an aqueous solution (1) of a salt of a second metal and a first acid, the first acid having a pKa of at least 1.5 at 25° C., to form an aqueous solution (2) comprising a salt of the second metal having cobalt carbonyl as anion,
(b) performing a first separation step (102) on the product (12) of step (a) which comprises separating the aqueous solution (2) from the organic hydroformylation reaction product to form an organic reaction product having a reduced cobalt content (13),
(c) performing a second demetalling step (103) comprising contacting the organic reaction product (13) separated in step (b), in the presence of an oxygen-containing gas or an oxygen-donating compound (7), with an aqueous solution (3) of a second acid to form (i) an aqueous solution (4) comprising a cobalt salt of the second acid and (ii) a cobalt-depleted organic reaction product (15), and
(d) recycling at least part of the aqueous solution (2) separated in step (b) to the hydroformylation reaction (200).

In the first demetalling step (a), a significant portion of the cobalt carbonyls are extracted into the water phase. In the second demetalling step (c), the remaining cobalt carbonyls are decomposed and the cobalt metal is recovered as an aqueous solution of its salt having cobalt as the cation. The second demetalling step is preferably an "air demetalling" step, as described above, which may be made very effective in reaching very low levels of cobalt in the organic product.

The advantage of performing the demetalling in two distinct and separate steps is that the equipment and process conditions for the two steps may be tailored separately from each other, to better suit the respective target reactions that are to occur in the two steps, and which are different. As a result, the two reactions may be optimised individually, which results in a more efficient overall process, in terms of equipment needs as well as in terms of effectiveness in recovering the catalyst metal.

The process according to the present invention comprises a low number of process steps for removing the cobalt catalyst from the hydroformylation product and recycling the catalyst to the hydroformylation reaction, its process steps may be individually optimised, leading to short residence times and thus to smaller equipment sizes, and in addition offers the opportunity to operate in a closed loop and with a water inventory that is very easy to maintain and control.

The resulting aqueous solution from the first demetalling step is highly concentrated in the catalyst metal and in particular in the carbonyl form thereof. We have found that direct recycle of this solution to the hydroformylation reaction may be performed without incurring a significant loss of volume efficiency in the hydroformylation reaction. A free water phase, when present in the hydroformylation reactor, will contain some of the cobalt, because reactions (1), (3), (4) and (5) are allowed to take place. At oxo conditions, all these reactions are fast and equilibrium is readily established, thereby partitioning the cobalt between the organic and the free water phase. The cobalt in the water phase is not available as catalyst to the olefin in the organic phase. The equilibrium however is strongly in favour of the cobalt carbonyl form, and more particularly of $HCo(CO)_4$, in the organic phase. The amount of cobalt that is inactive in the reactor, because it is caught in the free water phase, will therefore depend on the amount of water present. The smaller the amount of free water present, the smaller the amount of cobalt that is inactive in the reactor, and the less the reactor volume has to be compensated for the inactive volume consumed by the free water phase and for the catalytically inactive amount of cobalt that is present therein. The direct recycle in step (d) serves to avoid a complex intermediate extraction step to bring the carbonyls first into a suitable organic phase, as well as an even more complex and necessarily high pressure preforming step, upstream of such an extraction step.

We have also found that feeding cobalt catalyst that is already partly present as carbonyls to the oxo reaction avoids the induction time associated with the preforming reaction before the hydroformylation reaction may take place, an induction time that is particularly noticeable when processing olefin feeds containing small amounts of diolefins. We have found that the preforming reaction is autocatalytic, and that the preforming of $Co^{2+}$ is therefore characterised by an induction time, during which first an amount of cobalt carbonyls is formed which can then act as preforming catalyst and accelerate the preforming reaction. The presence of carbonyls already at the start of the preforming reaction significantly boosts the overall reaction rate, whether the preforming is performed separately or in the oxo reactor itself.

In a preferred embodiment, the process according to the invention further comprises the step of:
performing a second separation step (104) comprising separating the aqueous solution (4) from the cobalt-depleted organic reaction product (15) produced in step (c).

As a result of the more efficient second demetalling step, lower concentrations of the catalyst metal are left in the resulting organic reaction product. The catalyst metal is fully oxidised at this stage, and almost exclusively in the water phase. The metal in the organic reaction product is therefore almost exclusively present in the small amount of water that is entrained as a finely divided mist in the organic product. It is therefore preferred to provide a high performance organic/ water separation step for removing as much as possible of the entrained water from the organic product, such that a further washing step, typically included to catch and/or dilute the entrained water mist, may be eliminated or simplified. This brings the advantage that the water balance of the overall process becomes more simple and easier to control.

Optionally, at least part of the aqueous solution (2) of the salt of the second metal with the cobalt carbonyl anion from step (b) intended for recycling is first concentrated by removing water therefrom, using known techniques such as distillation, evaporation or reverse osmosis, and the concentrated aqueous solution is then recycled to the hydroformylation reaction in accordance with step (d). During this concentration step however, volatile $HCo(CO)_4$ may be formed, and this may create a problem of loss of carbonyls from the cobalt water to be recycled to hydroformylation, as well as limitations on where the removed water may be routed. A recycle water concentration step that is more advantageous will be discussed later.

In another embodiment, which is particularly preferred, the second metal is also cobalt.

This feature brings the advantage that more catalyst metal becomes available in the hydroformylation reaction. The oxo reaction conditions of temperature, pressure, partial pressures of hydrogen and carbon monoxide, in combination with the presence of metal carbonyl catalyst, are advantageous for the preforming reaction to occur, such that more of the useful cobalt carbonyls may be formed in the hydroformylation reaction zone, and may further contribute to the catalytic activity.

In a preferred form of this embodiment, the process of the invention comprises the step of recycling at least part of the aqueous solution (4) separated in step (e) as at least part of the aqueous solution (1) to the first demetalling step (a).

The advantage of this additional step is that less of the aqueous solution of the second demetalling step needs to be disposed of. It is preferred to recycle all of the aqueous solution (4) from the second separation step (e) to the first demetalling step (a), such that the disposal burden associated with this aqueous solution is eliminated.

Other and further objects and advantages of the present invention will become apparent from the more detailed description hereinafter.

DETAILED DESCRIPTION OF THE INVENTION

Figure 1:
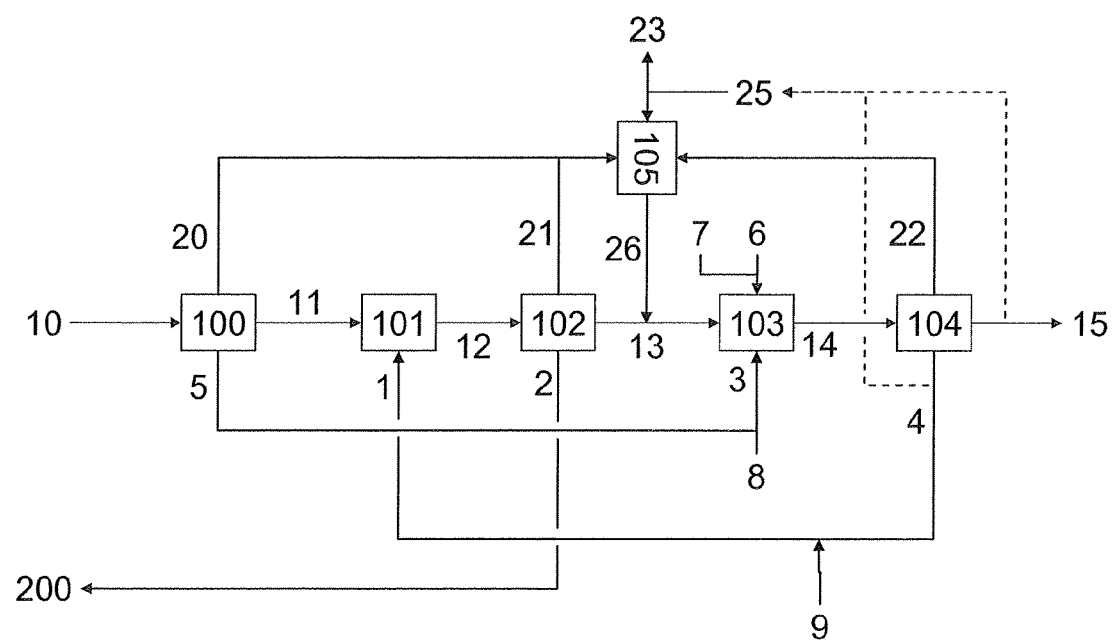
FIG. 1 shows a flow diagram of a hydroformylation catalyst cycle illustrating one of the preferred embodiments of the invention.

It has already been demonstrated by the "Kuhlmann" catalyst cycle that $HCo(CO)_4$, i.e. the main cobalt carbonyl species present under hydroformylation reaction conditions, behaves as a Brönsted acid and can be neutralised using a base. The present invention uses the capability of that (hydrido-) or (hydro-) cobalt carbonyl to dissociate in water as a Brönsted acid, thereby forming a cobalt carbonyl containing anion, but in a different way.

The purpose of step (a) of the current invention is to extract as much as possible of the cobalt carbonyl containing anion present in the organic hydroformylation product from that organic hydroformylation product and into a dilute aqueous phase that can be separated therefrom. This is accomplished by contacting the organic hydroformylation product with an aqueous solution of a salt of an acid, herein called the first acid, having a pKa of at least 1.5 at 25° C. The pKa of the first acid, defined as follows, and if a dibasic or polybasic acid is used it should be the first pKa of the acid, must be higher than the pKa of hydrocobalt carbonyl, which is believed to be 1.14 at 25° C.

$$pK_a = -\log_{10}[H^+][\text{anion}^-]$$

In principle, the salt of any acid fulfilling this requirement is suitable for the extraction of the cobalt carbonyl. However, because upon extraction of the cobalt carbonyl the first acid is reformed and much of this acid remains in the aqueous solution that is recycled to the hydroformylation reaction, we prefer to use acids of which the anion does not behave as too strong a base. We therefore prefer to use an acid having a first pKa of at most 7, preferably at most 6, more preferably at most 5, and most preferably at most 4. This offers the important advantage that such acids have little to no effect in the hydroformylation reaction, including preforming, where under conditions of hydrogen partial pressure and temperature the hydro cobalt carbonyl, i.e. the acidic form of the cobalt carbonyl, is restored. On the other hand, in the presence of the free water phase, acids stronger than hydrocobalt carbonyl, such as sulfuric acid, are considered harmful to the catalytic activity of the hydrocobalt carbonyl.

We prefer to use an organic acid as the first acid, because this typically avoids introducing heteroatoms into the process. Suitable acids are propionic acid ($pK_a=4.87$), acetic acid ($pK_a=4.75$) and formic acid ($pK_a=3.75$). Most preferred is formic acid, because formic acid, or a derivative thereof, is an expected component in the hydroformylation product, either as such or in the form of the formate ester of the product alcohol. The use of formic acid as the first acid therefore does not add a separate burden in the further treatment steps of the hydroformylation product, for the removal of the acid or of its ester. Formic acid brings the additional advantage of being less soluble in the organic phase, so that for the same acid concentration in the aqueous phases of the process, after phase separation less acid leaves the process with the cobalt-depleted organic reaction product. This reduces any acid make-up in case that would be required.

We have found that step (a) is preferably operated at a temperature of about 100° C., i.e. in the range of from 50-150° C., preferably 70-130° C., more preferably from 80 to 120° C., even more preferably from 90 to 110° C. and most preferably from 95 to 105° C. The pressure needs to be sufficient to prevent the water from boiling at the operating temperature. In addition, a higher pressure in step (a) may eliminate the need for pumps to perform liquid transfers downstream of step (a), except for effecting the recycle(s). We prefer to operate at a pressure in the range of about 2-15 bar gauge (barg), more preferably of 3-14 or 4-13 barg, even more preferably of 5-12 barg or 6-11 barg and yet more preferably of 6-10 barg, most preferably of 7-9 barg and typically around 8 barg. We typically may operate the first demetalling step (a), which is in essence an extraction and neutralisation step, as a single step in co-current mode with respect to the two liquid phases. However, counter-current operation may also be provided and is preferred because it overcomes the equilibrium constraint associated with a single co-current step. We prefer to operate with a weight ratio of aqueous solution to organic hydroformylation product of from 3 to 30%, preferably from 5 to 20%, more preferably from 7 to 16%, even more preferably from 8 to 14%, yet more preferably from 9 to 12% and most preferably from 9 to 11%, i.e. about 10%. We have found that the lower the water/oil ratio in step (a), in particular in counter-current mode, the more concentrated the cobalt carbonyl solution from the subsequent separation step (b) becomes, and the lower the amount of water that needs to be recycled to the hydroformylation reaction for the same amount of cobalt catalyst recycle. However, the solubility limits of the salts in that recycle catalyst solution, i.e. of the cobalt carbonyl salt and of the remaining salt of the first acid, should preferably not be exceeded, and thus also the minimum water-to-oil ratio in step (a) is preferably respected.

The aqueous solution feed to extraction step (a) preferably contains at least sufficient cations to extract all the cobalt carbonyl anions available in the hydroformylation reaction product before extraction. Assuming all cobalt is present as $HCo(CO)_4$, the stoichiometric amount of cations is equivalent to half the amount of cobalt present in the hydroformylation reaction product entering step (a). We prefer to operate without any excess, ideally, but because of control difficulties we may allow a stoichiometric excess in the range of 5-50%, preferably 6-30%, more preferably 7-20%, even more preferably 8-15%, yet more preferably 9-12%, most preferably about 10%. The salt concentration in the aqueous solution feed to step (a) preferably corresponds to the amount of cation required, taking into account that if a dibasic acid is used as the first acid, only the first dissociation should be accounted for. We have found that with a residence time of about 1 minute in a single step in co-current mode, as much as 75% of the cobalt can be extracted from the organic phase under these conditions. In multistage counter-current mode, the residence time may be higher, and the amount extracted may also be higher.

Step (a) of the process according to the invention is concerned with extracting the cobalt carbonyl species present that are able to behave as a Brönsted acid. Because also other cobalt species, including other cobalt carbonyls such as $Co_2(CO)_8$, are typically present in step (a), upon separation in step (b), the organic reaction product is expected to contain catalyst metal at levels sufficiently high to warrant further recovery.

Step (c) of the process of the invention has the purpose of recovering as much as possible of the catalyst metal remaining in the organic reaction product obtained from separation step (b), and the conditions thereof can be fully and independently targeted to that purpose alone.

A highly efficient method is to use "air demetalling" as described above, because it is highly effective and typically requires very low residence times, and thus low volumes of organic hold-up, which reduces safety concerns. We prefer to operate such "air demetalling" step by contacting the organic reaction product separated in step (b), in the presence of an oxygen-containing gas or an oxygen-donating compound, with an aqueous solution (3) of a second acid.

In the context of the invention, the second acid preferably also has a pKa of at least 1.5. The same pKa criteria as for the selection of the first acid preferably apply to this second acid.

The oxygen-containing gas may preferably be air, because that is typically more readily available. We prefer the air demetalling step to use a gaseous diluent, such that the gas compositions in the demetalling steps can be maintained above the upper flammability limit, and the risk of explosions may be minimised. Nitrogen or another inert gas may be suitable, but we prefer to use a flammable gas as the diluent, so that the resulting offgasses from this demetalling step are smaller in volume and remain suitable for combustion, such as in a furnace, even if these offgasses are the only fuel that is fed thereto. A suitable air demetalling step is disclosed in our copending patent application PCT/EP2008/053783, which published as WO 2008/128852.

Oxygen-donating compounds may also be used in the second demetalling step (c). Suitable candidates are peroxides, such as tertiary butyl hydroperoxide, and peracids. A particularly suitable compound may be $H_2O_2$, because it is more readily available and leaves only water as the byproduct after the oxidation, and therefore does not introduce an extra compound into the process. Many oxygen-donating compounds, upon donating an active oxygen atom as the oxidant, do not leave components that are gaseous under normal conditions. As a result, the second demetalling step using such oxygen-donating compounds does not generate an offgas stream, and thus does not create a need to dispose of any waste gas stream, unlike the case when air or another gaseous oxidant-containing stream is used. A drawback, if the oxygen-donating compound is introduced in a solvent, such as $H_2O_2$ dissolved in water, is the introduction of extra solvent or water into the catalyst cycle, which needs to be removed and disposed of or recovered. Because of its ready availability and low cost, air remains the most preferred reactant for the second demetalling step in a commercial environment.

We have found that in step (c) very effective demetalling can be achieved, reaching cobalt levels of 1 ppm wt or below in the organic product from step (c). In "air demetalling", we prefer to use conditions of 60-130° C., preferably 65-100° C., more preferably 80-95° C. and even more preferably 70-82° C. When hydrogen peroxide is used, we prefer to operate at a pressure sufficient to substantially avoid water vaporising. If an oxygen-containing gas is used, we prefer to operate at a pressure in the range of 1-15 barg, preferably 2-10 barg, more preferably around 7 barg at the point where the oxygen-containing gas is introduced, and around 2.5 to 3 barg at the point where the offgas is separated from the two liquid phases, or at a pressure sufficient to allow the offgas to be introduced into the site fuel gas system or into a furnace fuel gas line. A higher pressure helps to introduce oxygen into the liquid phases, in particular into the water phase, which is the more difficult as we believe oxygen favours to be in the organic phase. We also believe that oxidation of the acid used in the air demetalling step is a reaction that may be in competition with the desired oxidation of cobalt carbonyls. A fast transfer of cobalt carbonyls between water phase and organic phase may thus be desirable to enhance the desired cobalt oxidation reaction and minimise the undesirable loss of acid by oxidation. For the same reason, interfacial area between the different phases is preferably increased, such as by one or more static mixers or by having a packing provided in the equipment, or by agitation. High interfacial areas, in the range of 25-60 $cm^2/cm^3$, may already be achieved with the very convenient use of static mixers. This increases interfacial mass transfer without affecting the secondary oxygen consumption rate in side reactions. It therefore allows reducing the excess of oxygen-containing gas needed for the reaction, and allows achieving substantially complete transfer of the cobalt from the organic to cobalt salt in the water phase in about 40 seconds or less. We prefer to operate with a stoichiometric excess of the second acid relative to the amount of cobalt that is present in the organic feed to step (c), and more preferably with an excess in the range of 50-150%, even more preferably 60-120%. A typical residence time for the organic liquid in step (c) is in the range of 2-10 minutes, preferably 3-5 minutes, typically about 4 minutes. The oxygen or oxygen-donating compound is preferably also present in stoichiometric excess to the cobalt present, albeit more preferably avoiding too high an excess in order to limit side-reactions such as oxidation of aldehyde or of the acid, and in order to minimise equipment and energy requirements to provide the oxidant to the process. We prefer to operate with a stoichiometric excess in the range of 20-100%, more preferably 30-80% and even more preferably 30-70% or 30-50%. When the cobalt concentrations are low, such as below 1500 ppm by weight relative to the organic reaction product having a reduced cobalt content obtained from first separation step (b), it may be more convenient to operate at higher excess rates for acid and/or gas, in order to maintain good control capabilities. We have found that when the process according to the invention uses formic acid as the second acid and also as the first acid, that the process may be operated as a closed loop catalyst cycle. In addition, formic acid is formed as a byproduct in cobalt hydroformylation and/or from hydrolysis of formate esters, and we have found that the process may then be operated advantageously near to its acid equilibrium point, i.e. whereat the acid makeup is minimized or even eliminated because there is a balance between the amount of acid made in the process, such as in the hydroformylation step, with the amount of acid that is lost by oxidation together with the amount of acid leaving the cycle as dissolved in the cobalt-depleted organic reaction product. The acid equilibrium point of the overall cycle typically depends on the operating conditions in the hydroformylation reactors and in the demetalling section, and we have found that it may be reached when the aqueous solution from the second separation step contains between 0.5 to 1% by weight of free formic acid.

When using an oxygen-containing gas, for which air is most convenient, we also prefer to use a flammable diluent, such as natural gas or methane, to keep the air/diluent mixture above its upper flammable limit. More details are disclosed in our copending application PCT/EP2008/053783, which published as WO 2008/128852. We prefer this flammable gaseous diluent to be low in sulphur, such as less than 1 ppm by weight, so that oxidation of sulphur to water soluble sulfoxide and further to sulphate, and build-up thereof in the water loop of the process is minimised. Also, chlorine is desirably limited to a similar value.

As mentioned before, we prefer to perform and/or complete the optional second separation step (e) with the help of a coalescer, so that the amount of water entrained with the organic phase leaving the catalyst cycle, and which may still contain some cobalt, is minimised. A coalescer is a device that is employed to facilitate the separation of two liquid phases. A problem with separating two liquid phases can be that the density difference, which drives the separation, may be rather small. In this situation the smaller droplets travel slowly through the continuous phase (according to Stokes' Law) and in an empty vessel, they have to travel all the way to the bottom (or the top) before they start agglomerating (i.e. coalescing) to form larger droplets and ultimately separate out as a separate continuous phase. In a coalescer, horizontal (or substantially horizontal) baffles are provided within the vessel in order to reduce the distance the droplets must travel before they collect and can agglomerate, and thus make the separation more effective and volume-efficient. A preferred coalescer design comprises a drum with a number of parallel baffles inside, which are horizontal or slightly inclined from the horizontal. Small droplets will only need to travel to the baffle that is just below or above them, where they will collect with other droplets and form larger droplets (by coalescing with each other) which then may travel to the end of the baffle and from there will move with the faster speed (larger droplet) to the bottom or top of the vessel where the continuous separate phase is formed and removed through the outlet nozzle. The benefit of using a coalescer in the present invention is that the entrained water content of the cobalt-depleted organic reaction product will be reduced, if not eliminated. Any free water remaining in the organic product of step (e) may contain cobalt, which is then lost from the catalyst cycle and may cause problems downstream, e.g. in the subsequent hydrogenation step. Another embodiment of a coalescer may be one where the fluid containing small droplets of a different phase is pushed through a high porosity solid such as a packing or crinkle-wire-mesh-screen that is made of a material to which the droplet phase has a high affinity or wettability. The small droplets then tend to adhere to this easily wettable material and coagulate to form bigger droplets, which are then released from the material and readily separate into a continuous phase that can be drawn off. This embodiment may take the form of a filter, and may be included in the above described coalescer setup as a prefilter. We have found that it is advantageous to avoid an additional washing step, because this introduces diluent water into the catalyst cycle which then needs to be removed therefrom, typically incurring the consumption of more energy, and if the separated water cannot be recycled as wash water to the washing step, additionally creating a disposal problem.

It is understood that the demetalling reactions are competing with the formation of cobalt clusters, presumably according to reaction (6) as the first steps, but which include further derivative cobalt carbonyl compounds having more cobalt atoms and fewer CO fractions, down to a level where essentially only cobalt metal is present.

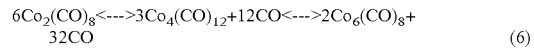

$$6Co_2(CO)_8 \longleftrightarrow 3Co_4(CO)_{12} + 12CO \longleftrightarrow 2Co_6(CO)_8 + 32CO \quad (6)$$

The solubility of these cobalt carbonyl compounds in the organic phase reduces as they contain fewer and fewer CO fractions in the molecule, to the point that the species come out of solution and form solid particles. While the $Co_4(CO)_{12}$ is still considered as oil-soluble, the next form $Co_6(CO)_8$ is considered as being for practical purposes insoluble. These particles may deposit or adhere to parts of the equipment, and often build up as a shiny metal layer recognised as "cobalt plating".

We have found that these cobalt clustering and/or plating reactions are characterised by high activation energy relative to the demetalling reactions shown hereinbefore, such as at least 40 kcal/mole. We therefore prefer to use the demetalling steps that are operated at lower temperatures, such as "air demetalling", above "airless demetalling" which needs higher temperatures of typically 140-190° C., more particularly about 164° C. We also have found that it is preferable to operate the demetalling step, especially any higher temperature airless demetalling but also including a lower temperature air demetalling step, under a minimum partial pressure of 0.2 MPa of CO, such that the cobalt carbonyl decomposition reactions and the plating reactions (6) are pushed sufficiently to the left, or even inhibited, and more cobalt ends up as $Co^{2+}$. These demetalling steps are preferably operated with an interfacial area between water and organics of at least 60 $cm^{-1}$, more preferably at least 100 or 150 $cm^{-1}$, even more preferably at least 200 $cm^{-1}$, yet more preferably as high as 380 $cm^{-1}$ or more, up to 2000 $cm^{-1}$. This interfacial area should be created from the moment the feeds are subjected to conditions where the carbonyls are unstable (high temperature, low CO partial pressure, introduction of the oxygen or oxygen-donating compound) in order to increase the selectivity to $Co^{2+}$. While cobalt cluster formation may be minimised, it may not be totally avoided. By providing strongly turbulent flow in the demetalling step, the particles that are formed may be carried with the turbulent flow downstream to a separator or settler, where the gas, water and organic phases are allowed to settle and separate, and where solid deposits are less of a nuisance and are allowed to buildup before the equipment performance is impaired. Such cobalt deposits, including "cobalt plating", in the demetalling section can be removed chemically as explained in WO2005/058787 as a method for cleaning the hydroformylation reactors, provided the demetalling equipment is made of suitable construction materials that are able to withstand the aggressive nature of the chemicals used in this cleaning process. For details on suitable construction materials, we also refer to WO2005/058787. The cleaning requires the equipment to be taken out of service, and therefore it is preferred to have the solids depositing at locations in the process equipment where the process performance is less readily impaired by them. This reduces the cleaning frequency and therefore increases equipment availability. Alternatively, the solids are collected in equipment that may be taken out of service without having to stop the process, such that equipment availability is not reduced.

In order to increase turbulence, we prefer to have some amount of additional gaseous components present in the demetalling step. The addition of air in the "air demetalling step" is therefore highly advantageous, especially when an extra volume of diluent is used as described below. If insufficient gas is available from the flashing of the liquids because of the pressure letdowns from upstream, additional gas may be added in. Any gas streams are suitable for this purpose, but portions of one or more of the offgas streams that may be separated at higher pressure levels from the hydroformylation reaction product before the demetalling step are particularly suitable. We prefer to use slipstreams from the offgasses coming from an intermediate pressure separator and/or from a high pressure separator that may be operated between hydroformylation and demetalling. Static mixers may also be used to increase turbulence, either alone or in combination with the addition of gas.

The "air demetalling" introduces air into a closed system full of flammable materials. It does therefore raise a safety concern. This is readily controllable in steady state operation, but needs special precautions for unsteady operations, such as with process upsets, grade switches, and the like. How these problems may be resolved is described in detail in our co-pending patent application PCT/EP2008/053783, which published as WO 2008/128852.

The second demetalling step (c) according to the invention requires the presence of a second acid. Many acids are suitable, but we prefer to use organic acids. Suitable organic acids are propionic acid, acetic acid and formic acid. We prefer to use an acid that is less soluble in the organic phase, because less acid is then removed from the demetalling step with the metal-depleted organic reaction product. We therefore prefer to use acetic acid or formic acid, but most preferably formic acid because of its lower solubility in the organic reaction product. Formic acid is a byproduct from the hydroformylation reaction, because also formate esters are formed in hydroformylation, and upon hydrolysis, these formate esters may generate formic acid as a byproduct. The process steps and equipment downstream of hydroformylation are therefore routinely adapted to handle the presence of formic acid and formate esters in the hydroformylation reaction product. Other acids and/or their esters would create extra process burdens and extra product quality concerns. We therefore prefer to use formic acid as the second acid in the second demetalling step (c).

In a preferred embodiment, the second acid used in the second demetalling step (c) is the same as the first acid in the first demetalling step (a). The advantage is that the overall process needs only to be adapted for handling one acid and one kind of ester, and not two different acids and/or esters. This simplifies process equipment, selection of materials of construction, and any waste stream handling steps that may be necessary.

In another embodiment of the invention, the second metal in demetalling step (a) is the same as the first metal (that is, the metal of the carbonyl compound comprising the hydroformylation catalyst). The second metal may thus also be cobalt. We have found that in this embodiment, and when a second separation step (e) is included in the process, it is suitable to recycle at least part of the aqueous solution (4) of the cobalt salt of the second acid, produced in the second separation step (e), to the first demetalling step (a). In a preferred embodiment, the total amount of aqueous solution produced in step (e) is made available for recycle to step (a). In one alternative, at least a portion of the part of this aqueous solution from step (e) that is provided for recycle, which may be all of it, is first concentrated by removing water from the stream by means known in the art, such as distillation, evaporation, membrane separation and the like. A similar concentration or water removal step may be provided as an alternative to or in combination with the above mentioned concentration or water removal step, with regard to the aqueous solution produced in separation step (b) that is provided for recycle in step (d) to the hydroformylation reaction. Such water removal steps may be used and tuned to maintain a constant water balance in the overall process comprising the hydroformylation and the demetalling, and any optional wash steps that may be provided but which each time add water into the overall process. The better place to remove any excess water from the system is from the recycle stream (4) that flows from the second separation step (e) to the first demetalling step (a), because in this stream the concentration of cobalt carbonyls should be the lowest, such that the risk of the volatile and valuable $HCo(CO)_4$ also being removed at the same time is the lowest. Water removal from the recycle stream to the hydroformylation reactor is also suitable, but less preferred because the risk of also removing $HCo(CO)_4$ is higher.

Make-up hydroformylation catalyst may need to be introduced into the process, e.g. when the catalyst concentration needs to be increased, or when a part of the catalyst has been lost from the process or deposited inside the equipment and needs to be replaced. We have found that in the process according to the invention such a make-up of catalyst metal is most conveniently provided as a water soluble salt of the cobalt with a third acid, and this is preferably added into the part of the aqueous solution that is recycled from separation step (e) to the first demetalling step (a). If any of the recycle streams to step (a) or to the hydroformylation reaction do not recycle all the amount of the stream that is available, and thus part of any of those streams is discarded, there is a continuous withdrawal of catalyst metal from the process. This will cause a decrease of the catalyst concentration in the hydroformylation reaction and catalyst cycle system, unless a regular discontinuous or a continuous make-up of catalyst is provided. Such make-up is preferably added as just explained here. However, it is understood that other conventional alternatives for cobalt catalyst make-up are also suitable. Examples are the introduction of organic soluble cobalt salts, such as cobalt oleate, stearate, palmitate, naphthenate, or cobalt tallate, or cobalt hofate, wherein the hofate is the term used when using the heavy acids formed in the oxo process by e.g. the Cannizarro reaction or the direct carbonylation of the olefin with water and CO, or by aldehyde oxidation. Other more complex make-up options involve other cobalt compounds, such as $CoCO_3$, $CoSO_4$, or more typically $Co_2O_3$. These may be preformed in a separate preforming reactor before the resulting carbonyls are fed to the hydroformylation reaction.

It may occur that an undesired metal finds its way into the process streams, such as by corrosion of the equipment or by introduction as a trace element in any of the feed streams. Such a metal may then convert to a water soluble form in any of the demetalling steps, and possibly impair the reactions that the catalyst metal is supposed to participate in. In such circumstances, a portion of any of the water streams containing this undesired metal, but also the catalyst metal, may need to be removed from the system, either occasionally or as a continuous slipstream. This may create another need for more make-up of the catalyst metal, preferably as explained above. A similar problem is created if an unsuitable or disturbing water-soluble anion is introduced into the water streams of the catalyst cycle.

As the third acid, many acids are suitable, but we prefer to use an acid having a pKa of at least 1.5 at 25° C. The same pKa criteria as for the selection of the first acid preferably apply to this third acid. With such an acid, the make-up metal salt is able to participate in the first demetalling step (a) of the process. We prefer to use an organic acid as the third acid, such as propionic acid, acetic acid or formic acid. We prefer this third acid to be the same as the first acid, such that there is no interference between different acids in extraction step (a). Most preferred is that the first, the second and the third acid are all the same. These acids then are preferably all propionic acid, acetic acid, or formic acid. Acetic acid and formic acid are more preferred, and formic acid is most preferred because it is indigenous to high pressure cobalt hydroformylation processes, and because of its better solubility characteristics as already mentioned before. However, when the first acid and the second acid are both formic acid, we prefer to use acetic acid as the third acid because the cobalt salt thereof is more readily available and because cobalt acetate is more soluble in water than cobalt formate, and the amount of water introduced with the cobalt make-up can thereby be minimised. We have found that typically the amounts of acetic acid introduced as cobalt acetate are reasonably low, and when introduced into a process using formic acid in its demetalling steps, because of the higher affinity of acetic acid to the organic phase as compared to formic acid, such amounts are conveniently and sufficiently quickly removed from the process with the cobalt-depleted organic reaction product.

In the process according to the invention, step (d) recycles the aqueous solution comprising the metal salt of the cobalt carbonyl to the hydroformylation reaction. In one embodiment, we prefer that the amount of aqueous solution (2) comprising the salt of the second metal with the cobalt carbonyl anion recycled in step (d) to the hydroformylation reaction is at least 3% and at most 30% by weight based on the weight of the olefin feed to the hydroformylation reaction. It is preferred to avoid excessive amounts of water passing through the hydroformylation reaction, because it reduces the volume available for the organic phase in which the reaction occurs, and thus reduces the volumetric efficiency of the hydroformylation reactor, but also pulls more cobalt away from the organic phase where the reaction occurs. We prefer to assure that there remains a free water phase present at all times in the hydroformylation reaction and throughout the entire hydroformylation reactor, but we prefer to minimise the amount of free water present for the reasons explained. It should be understood that water is typically scarcely soluble in many feedstocks that may be hydroformylated, such as higher olefins in the $C_4$-$C_{14}$ range, but that typically the water solubility of the corresponding hydroformylation products is significantly higher. The organic phase in the hydroformylation reaction therefore develops a higher affinity for water as the reaction proceeds, and more water may become dissolved. We prefer to add sufficient water, preferably via recycling sufficient aqueous solution in step (d), such that there remains a free water phase present even in the hydroformylation reaction product. This brings the advantage that any species present in the hydroformylation reaction, and which are strictly water soluble and would precipitate without a free water phase present, may remain in solution throughout the oxo reaction. We prefer therefore to use an amount of water that is also above the solubility of water in the organic product of the hydroformylation reaction. This preferred minimum amount of water depends on the carbon number of the alcohol produced, with lower carbon number alcohols needing more water because of the higher solubility of water in their oxo product. We prefer that the amount of aqueous solution (2), comprising the salt of the second metal with the cobalt carbonyl anion, that is recycled in step (d) to the hydroformylation reaction is at least 3% and at most 25% by weight based on the weight of the olefin feed to the hydroformylation reaction, more preferably from 4% to 20%, even more preferably from 5 to 15%, most preferably from 6 to 13%, such as from 7 to 12%, and typically about 10%.

We prefer to cool the hydroformylation reaction product, which is typically at a temperature of from 150-200° C. at the end of the reaction, down to a temperature of from 30-60° C., and we prefer to perform this cooling while the product remains at high pressure. We have found that when there is free water present in the hydroformylation reaction product, cobalt carbonyls dissolved in this water phase are driven by this cooling step into the organic phase, and the cobalt concentration in the water phase may drop significantly. This effect is more pronounced at a higher pressure.

When a free water phase is present in the hydroformylation reaction product, we prefer to remove most of this free water phase before the hydroformylation reaction product enters the first demetalling step (a) of the process of the invention. The invention therefore provides a process further comprising performing a preliminary separation step (100) prior to step (a) comprising separating free water (5) from the hydroformylation reaction product (10) to form the catalyst containing reaction product (11) for the contacting in the first demetalling step (a).

In a further embodiment, we prefer to operate this step (g) under a partial pressure of carbon monoxide of at least 1.5 bar, preferably at least 2.5 bar, and more preferably at least 3 bar. Typically this step (g) operates at a pressure of 10-100 barg, and preferably of at least 15-20 barg, to avoid the need to provide additional liquid pumps downstream. Because of the amount of CO coming with the reaction product, the partial pressure of CO in step (g) is typically at least 7 bar, preferably at least 10 bar. This brings the advantage that the disappearance of carbonyls of the catalyst metal, according to optionally reaction (1) but in particular reaction (3) is minimised during the separation step (g), such that more of the metal carbonyl may be available for extraction in the first demetalling step (a). Also cobalt plating according to reaction (6) is thereby reduced.

In a further embodiment, when separation step (g) is present, the invention preferably provides a process comprising (h) using at least part of the free water separated in step (g) as water for the aqueous solution (3) of the second acid that is employed in second demetalling step (c).

We prefer to use all the water separated in step (g) as water for the aqueous solution (3) of the second acid employed in second demetalling step (c). As an alternative, only part of this water from (g) may be used in step (c) and another part may be introduced into the first demetalling step (a). Either alternative provides the advantage that all cobalt carbonyls present in the water separated in step (g) are either available for extraction in step (a) or are available for conversion to a metal salt in step (c). We prefer the alternative where all the water (5) separated in step (g) is directed to step (c), because this reduces any dilution of the aqueous carbonyl solution (2) that is separated in step (b) and recycled in step (d) to the hydroformylation reaction.

The first demetalling step (a) according to the invention may comprise at least one co-current contacting stage. Such a setup incurs a lower investment and is easy to operate, but its extraction is limited by the one stage equilibrium. Alternatively or in combination, the first demetalling step (a) may also comprise at least one counter-current contacting stage. In total, there may be provided at least 2, 3, 4, or even 5 contacting stages. The first demetalling step may be provided as an extraction tower, which may readily have a plurality of stages, possibly in an even larger number such as 7, 10, 12 or as much as 15 or 20 stages. Such an extraction tower is preferably operated in counter-current mode. This setup requires a higher investment, with more pumps, and is more difficult to operate and control. As it is not limited to a single stage equilibrium, it may be able to achieve a higher level of extraction, and provide a more concentrated aqueous product.

One form of cobalt carbonyl, i.e. $HCo(CO)_4$, is known to be volatile. As a consequence, offgas streams separated from liquid hydroformylation reaction products containing cobalt carbonyls, may also contain cobalt carbonyls. Offgasses separated at high pressures, such as 200 barg or above, typically contain only small traces, if any, of cobalt carbonyl. We have found that the offgasses separating off at lower pressures may contain sufficient cobalt carbonyls to create problems downstream, primarily by depositing in undesirable locations and impairing operations. In addition to the desire to recover such cobalt carbonyls for recycle to the hydroformylation reaction, it is equally desirable to remove these cobalt carbonyls from these offgasses before such offgasses find further use.

The process of the invention may separate an offgas stream in many locations, such as in any of steps (a), (b), (c), (d), and, when present, also in (e) and possibly in (g). The invention therefore further provides a process which comprises separating at least one volatile cobalt carbonyl-containing offgas stream in any of the steps (a), (b), (c), (d) and, when present, (e) and (g), which further comprises (j) performing a first absorption step (105) comprising contacting at least part of at least one of said separated offgas streams with a first absorption liquid (25) for absorbing at least part of the volatile cobalt carbonyl present in said offgas stream, thereby forming a cobalt-containing first absorption liquid (26).

More details and advantages about a suitable process for this first absorption step may be found in our copending patent application U.S. Ser. No. 61/092,835.

Several offgas streams may preferably be combined, such as the offgas streams originating from steps (a), (b) and (g). The offgasses from steps (c) and/or (e) may be already free of cobalt, and may contain oxygen, in which case we prefer to not combine these with the cobalt containing offgas streams from the upstream steps. The advantage of this first absorption step is that the offgas stream after the contacting is essentially free of volatile cobalt carbonyl, which otherwise could foam solids, such as $Co_2(CO)_8$, $Co_4(CO)_{12}$, or cobalt clusters wherein even more cobalt atoms are combined with a relatively lower number of CO molecules. Such solids may then deposit on the inside walls of the process equipment and thereby impair the operations, such as by fouling control valves or burner tips, blocking connections to pressure measurements or flow measurement devices, and the like.

In an embodiment, the process of the invention further comprises:

(k) adding the cobalt-containing first absorption liquid (26) from the first absorption step (j) to the first demetalling step (a), the first separation step (b) or the second demetalling step (c).

In this embodiment, the cobalt absorbed from the offgas is recycled into the catalyst cycle, and the cobalt is recovered. We prefer to add the cobalt-containing first absorption liquid (26) from the first absorption step (j) to the second demetalling step (c) or the first separation step (b), and even more preferably to the first demetalling step (a), because, if the cobalt absorbed into the liquid remains present in a carbonyl form, at least part of this cobalt carbonyl may be recovered as the carbonyl form, and added to the cobalt carbonyls that are recycled to the hydroformylation reaction in step (d), upon which it is readily available as catalyst without first needing to be reconverted into the carbonyl form. However, if the amount of cobalt in the absorption liquid is low, we prefer to route the cobalt-containing first absorption liquid (26) from the first absorption step (j) to the second demetalling step (c). This avoids introducing an extra organic volumetric load into the first demetalling step (a), which is an extraction step and therefore may be negatively affected by a higher oil/water ratio.

We have found that not all liquids are equally suitable for use as the first absorption liquid (25) in this first absorption step (j). We prefer to select as first absorption liquid a liquid characterised by having a vapour-liquid distribution coefficient for hydrocobalt tetracarbonyl at a temperature of 80° C. of at most 3.0, expressed as gmol/l of $Co^{-1}$ in the vapour divided by gmol/l of $Co^{-1}$ in the liquid. Preferably we employ a first absorption liquid having a vapour-liquid distribution coefficient of at most 1.5, more preferably at most 1.0, even more preferably at most 0.6 and yet more preferably at most 0.1, expressed in the same units and at the same temperature.

The vapour-liquid distribution coefficient of a particular liquid for hydrocobalt tetracarbonyl may be determined, and we prefer to use the following method. A continuous hydroformylation reaction is operated in steady state with a Cobalt Flash stripper-reactor downstream thereof for stripping $HCo(CO)_4$ from the oxo product. The cobalt-containing vapour stream from the stripper-reactor contains a steady concentration of cobalt as $HCo(CO)_4$ that may readily be analysed for and expressed in gmol/l. The vapour stream is bubbled through a scrubber vessel containing the absorption liquid and kept at the prescribed measuring temperature of 80° C. The vapour stream from the scrubber vessel is led to an absorber tower or vessel for absorption of any cobalt remaining therein. The cobalt in this vapour from the scrubber vessel is also present as $HCo(CO)_4$ and its concentration may also be analysed for. An equilibrium is reached when the two vapour streams contain the same cobalt concentration and the absorption liquid in the scrubber vessel is saturated with $HCo(CO)_4$. The liquid is then sampled and analysed for its cobalt content as gmol/l. The ratio of the cobalt concentrations in the vapour divided by that in the liquid gives the "apparent" vapour-liquid distribution coefficient for hydrocobalt tetracarbonyl, for this particular absorption liquid and at the temperature of measurement. A lower "apparent" distribution coefficient is obtained at a lower temperature. It is therefore preferred to operate the absorption step (j) at a temperature in the range of 10-100° C., preferably 20-90° C., more preferably 25-80° C., yet more preferably 30-70° C. and even more preferably 35-60° C.

We have found that the first absorption liquid may be organic. We prefer to use as organic absorption liquid an organic liquid that is already present in, or related to the hydroformylation process according to the invention, thereby avoiding concerns of the process being contaminated with unfamiliar streams or species.

In one embodiment, we prefer that the absorption liquid in step (j) is a part of the cobalt-depleted organic reaction product formed in step (c). This stream is most readily available and recycling part of this cobalt-depleted organic reaction product over the absorption step and into either the first demetalling step (a), the first separation step (b) or the second demetalling step (c) creates a fairly short organic recycle loop with the least effect on the additional hydraulic loads of the equipment items, in particular of any downstream steps as described further herein. We prefer that this recycled cobalt-depleted organic reaction product is essentially free of oxidant, such as dissolved air or hydrogen peroxide. This reduces the likelihood that cobalt carbonyls, possibly after becoming absorbed into the liquid, become quickly converted to non-carbonyl cobalt species, and maximises the potential recovery of the absorbed cobalt carbonyls for recycle as cobalt carbonyls to the hydroformylation reaction in step (d). In the alternative wherein the cobalt-containing absorption liquid from step (j) is routed to the second demetalling step (c), the presence of an oxidant in the absorption liquid of step (j) is not a burden and may be preferred because of its beneficial effect on the "apparent" distribution coefficient by readily converting volatile cobalt carbonyl to non-volatile cobalt species.

In another embodiment, we prefer to use, as first absorption liquid in the first absorption step (j), an organic liquid that is generated further downstream from the second demetalling step (c).

The invention therefore further provides a process wherein the cobalt-depleted organic reaction product is separated into at least a light hydroformylation fraction and a heavy hydroformylation fraction and the absorption liquid in step (j) is at least a part of the light hydroformylation fraction or of the heavy hydroformylation fraction. These light and heavy hydroformylation fractions bring the advantage that they are less prone still to contain any remaining oxidant, if such oxidant is used in the second demetalling step (c). We prefer to use the heavy hydroformylation fraction, because this is less volatile than the light hydroformylation fraction, and thus less of the organic first absorption liquid is vaporised and carried with the offgas from the first absorption step (j). The use of this heavy fraction also minimises the energy requirement associated with this organic recycle in the overall alcohol production process, as compared to the use of a lighter stream that is separated by evaporation.

The cobalt-depleted organic reaction product produced in the second demetalling step (c), or at least part of it, is typically subjected to a hydrogenation step, wherein typically aldehydes and/or formate esters are converted into alcohols. This hydrogenation may be performed on the cobalt-depleted organic reaction product itself, or a part thereof, but it may also be performed on a stream obtained by first separating a light and/or heavy hydroformylation fraction therefrom. The hydrogenation step may be preceded by an additional washing step, to remove the last traces of catalyst metal, by a hydrolysis step, to convert formate esters and/or acetals by hydrolysis into alcohols and/or aldehydes, and/or by one or more distillation steps to e.g. separate aldehydes from the stream prior to hydrogenation, for instance for conversion of such aldehydes into carboxylic acids or to separate unreacted olefin molecules and recycle these to the oxo reaction.

The invention therefore further provides a process wherein the absorption liquid in step (j) is a part of a hydrogenation product formed by hydrogenating at least part of the cobalt-depleted organic reaction product formed in step (c).

The hydrogenation step may be followed by distillation of the hydrogenation product into different fractions. We have found that also these fractions are suitable as first absorption liquid in the first absorption step (j). The invention therefore further provides a process further comprising hydrogenating at least part of the cobalt-depleted organic reaction product from step (c) to form a hydrogenation product, separating at least part of the hydrogenation product into a light hydrogenation fraction and a heavy hydrogenation fraction and wherein the absorption liquid in step (j) is at least a part of the light hydrogenation fraction or of the heavy hydrogenation fraction.

We have found that the first absorption liquid may also be aqueous. Water may be used, but we have found that the absorption of cobalt carbonyls with water may be improved by providing a metal cation. The invention therefore further provides a process wherein the first absorption step (j) uses as the absorption liquid (25) an aqueous solution of a metal salt of a fourth acid having a pKa of at least 1.5 at 25° C. The same pKa criteria as for the selection of the first acid preferably apply to this fourth acid. By selecting a salt of such suitable acid, the $HCo(CO)_4$ from the gas phase is neutralised by the salt and forms the salt of the cobalt carbonyl, highly soluble in the water phase, plus the weaker fourth acid. As a result, there is little free $HCo(CO)_4$ in the water phase, and there is thus little impediment for more $HCo(CO)_4$ to absorb from the gas phase into the water phase.

The cobalt-containing absorption liquid from step (j) is preferably added to the first demetalling step (a), the first separation step (b) or the second demetalling step (c), as explained above. We therefore prefer that the fourth acid is the same as the first acid. This avoids the introduction of another and different acid into the catalyst cycle. Alternatively or in combination, we prefer the metal of the salt in the aqueous absorption liquid to be the same as the second metal of which the salt of the first acid is used in the first demetalling step (a). This avoids further contamination of the catalyst cycle with another and different metal. In our preferred embodiment, the salt in the aqueous absorption liquid is the same as the salt used in the first demetalling step (a). This embodiment avoids any contamination of the catalyst cycle with another and different metal as well as with another and different acid.

In a further embodiment, the invention provides a process wherein a part of the aqueous solution (4) of the second acid, formed in the second demetalling step (c) and preferably separated in the optional second separation step (e), is used as the first absorption liquid (25) in the first absorption step (j). In this embodiment, because of the possible presence of left-over oxidant, the absorption liquid coming from step (j) is preferably routed to the second demetalling step (c).

The process according to the invention is suitable for combination with the "Cobalt Flash" catalyst cycle mentioned above, in particular with the operating mode described in U.S. Pat. No. 5,237,105 (Summerlin) that is more suitable for the hydroformylation of olefin feeds having a higher average carbon number, such as at least 7, in particularly at least 8 or even 9.

The invention therefore further provides a hydroformylation process using cobalt as the hydroformylation catalyst wherein the first demetalling step (a) further comprises (l) contacting the cobalt catalyst-containing reaction product with a stripping vapour to form a cobalt carbonyl-containing stripping vapour.

Because the process according to the present invention brings its own recycle of cobalt carbonyls to the hydroformylation reaction in step (d), and the combination reduces the stripping duty of the cobalt stripping step of the "Cobalt Flash" cycle, the combination may represent a significant capacity increase to an existing "Cobalt Flash" catalyst cycle without having to revamp the stripping and absorption steps of such "Cobalt Flash" catalyst cycle. Because the bottom of the stripper reactor is such a combination allowed to contain remaining cobalt carbonyls, which are removed in subsequent demetalling step (c), less acid and/or less interfacial area are required for maintaining an acceptable operation of the stripper reactor, allowing a potential saving on the use of chemicals, stripping gas, and/or energy consumption. In addition, the additional preformer step that is provided in the "Cobalt Flash" catalyst cycle may be dispensed with and by using a coalescer in the separation step (e) also the typical wash tower as well as the evaporator of a typical Cobalt Flash catalyst cycle may possibly be dispensed with.

In one embodiment of this combination with "Cobalt Flash", the stripping vapour in the first demetalling step (a) comprises carbon monoxide and/or hydrogen. The carbon monoxide may help in keeping the cobalt in the carbonyl form, and the hydrogen may help in keeping the cobalt carbonyl in the form of the volatile $HCo(CO)_4$.

The contacting with the stripping vapour in the first demetalling step (a) may be performed in at least one co-current stage and/or in at least one counter-current stage.

The cobalt carbonyl-containing stripping vapour from the first demetalling step (a) is not very suitable for recycle to the hydroformylation reaction as such, because it is typically at a lower pressure and upon compression to the much higher hydroformylation pressure, the cobalt carbonyl will show a tendency to form solids that are prone to deposit in any compression device. The invention therefore provides a preferred embodiment of the process further comprising:

(m) performing a second absorption step comprising contacting the cobalt carbonyl-containing stripping vapour with a second absorption liquid to form a cobalt-containing second absorption liquid.

This second absorption step (m) may preferably be performed in an absorption tower.

The second absorption liquid preferably has the same characteristics as the first absorption liquid described above.

As second absorption liquid, however, we prefer to use an organic liquid. We have found that this is more convenient for recycling to the hydroformylation reaction. In one embodiment, the second absorption liquid comprises at least a part of a light byproduct or a heavy byproduct from the hydroformylation reaction and/or from a hydrogenation reaction downstream therefrom.

We have found however in addition that the absorption is more efficient when the second absorption liquid comprises an unsaturated hydrocarbon compound. We have found that such compounds show a higher affinity for the cobalt carbonyl that needs to be absorbed. In a preferred embodiment therefore, the second absorption liquid comprises at least part of the olefin feed. Optionally the second absorption liquid comprises a heavier olefinic absorbent, such as disclosed in U.S. Pat. No. 5,237,104 (Summerlin).

In a more preferred embodiment, the cobalt-containing second absorption liquid is directed to the hydroformylation reaction. In this embodiment, even more of the cobalt catalyst is recycled to the hydroformylation reaction in the carbonyl form, readily available to participate as active catalyst without the need to first form the cobalt carbonyl.

In the stripping step of the "Cobalt Flash" process, we have found that besides cobalt carbonyl, also water and lighter hydrocarbons are stripped from the hydroformylation product and carried out of the stripper-reactor step with the stripping gas. As discussed in for example U.S. Pat. No. 5,218,134 (Nadler et al.), a part of this water and hydrocarbons are typically condensed and recycled as liquid to the stripper-reactor of the Cobalt Flash process, optionally as a reflux to the stripper-reactor tower. We have found that in particular the organics condensing from this cobalt-loaded stripping gas may contain a high concentration of cobalt, typically in the form of organic soluble carbonyls. We have found that it is significantly advantageous to pump at least part of these condensed organics directly to the hydroformylation reaction, rather than recycling all to the stripper reactor. Preferably all condensed organics are pumped to the hydroformylation reaction. In a further embodiment the invention provides for a process wherein steps (l) and (m) are present and wherein the cobalt-containing stripping vapour from step (l) is, prior to the second absorption step (m), cooled and cobalt-containing organics are condensed out, at least part of said cobalt-containing organics being pumped to the hydroformylation reaction, and wherein optionally also water is condensed out, and at least part of said condensed water is also recycled to the hydroformylation reaction.

This additional recycle of cobalt carbonyls to the hydroformylation reaction significantly increases the availability of cobalt catalyst in a hydroformylation reaction operating with the Cobalt Flash catalyst cycle, and this effect is achieved irrespective whether it is in combination with the process of the current invention. This effect may be further enhanced by adding a chiller to the overhead of the stripper reactor, such that more of the hydrocarbons can be condensed, but also because it allows to operate the absorber tower at a lower temperature such that its performance is improved, and less absorption liquid is carried with the gas return from the absorber tower to the stripper reactor. In particular when the second absorption liquid comprises at least part of the olefin feed, the entrained olefin by-passes the hydroformylation reaction and this last advantage thus improves the overall yield of oxygenates produced per unit of olefin feed that is used. Overall, this mode of operation also reduces the duty on any preforming reactor as part of a Cobalt Flash catalyst cycle. The water condensed with these organics may be at least partly recycled to demetalling step (a). A further enhancement of the above effect may be achieved by pumping also at least a part of the water that is condensed by cooling and optionally chilling the stripper-reactor overhead, to the hydroformylation reaction, because of its cobalt and primarily cobalt carbonyl content. Optionally, this recycle is combined with the recycle of carbonyl in step (d) of the current invention. Preferably all of the condensed water is recycled. As an alternative, at least part of this condensed cobalt carbonyl containing water may be recycled to step (a), so that the carbonyls are extracted for recycle in step (d).

We have found that in the process according to the invention, the second demetalling step (c) may conveniently be performed in the presence of hydrogen peroxide, which may act as the oxidant. This brings the advantage that the second demetalling step is fast because of the oxygen presence, and thus may be operated with less energy input, as described above, but without creating an offgas stream that needs to be disposed of. The further advantage is that the leftover species from the oxidation with hydrogen peroxide is only water. The second demetalling step (c) may comprise at least one co-current contacting stage, and/or at least one counter current contacting stage. We prefer that the second demetalling step (c) comprises at least one co-current contacting stage. We have found that one single co-current contacting stage may be sufficient to achieve the desired low levels of catalyst metal in the cobalt-depleted organic reaction product formed in step (c).

The aqueous solution (4) of the cobalt salt of the second acid farmed in the second demetalling step (c) may become relatively concentrated, and we prefer to keep this aqueous solution at sufficient temperature and the salt level below the concentration at which the salt would come out of solution. We have found that water may unintentionally be removed from the catalyst cycle according to the invention, such as by water contained in the offgas vapours, withdrawal of parts of the aqueous solutions formed in steps (a) and (c) of the process, and/or water dissolved in the cobalt-depleted organic reaction product. We have found that in particular, the amount of water dissolved in the organic reaction product may be significant. There may therefore be a need to make up water into the process of the invention. We prefer to add such make-up water to the second demetalling step (c), because it helps to reduce the risk of salt coming out of solution in the aqueous solution (4) formed in step (c).

For similar reasons, any of the acids used in the process according to the invention may be withdrawn or leave the catalyst cycle, and a make-up of an acid may have to be provided to enable steady-state operation. We prefer to add such acid make-up also to the second demetalling step (c), as it is the most convenient location where the acid may readily participate in the demetalling reactions.

The process according to the invention is further illustrated by the flow diagram in FIG. 1, showing a preferred embodiment. In FIG. 1 the hydroformylation reaction product 10, comprising cobalt carbonyl as the dissolved catalyst, preferably after cooling and separation of the high pressure offgas, enters a separator 100 for performing the preliminary separation step (g). Free water 5 is separated from the cobalt carbonyl containing hydroformylation reaction product 11, which is directed to contactor 101. Also an offgas stream 20 may be formed and separated in separator 100. In contactor 101 the first demetalling step (a) is performed by contacting the product 11 with an aqueous solution of cobalt formate 1 taken as aqueous solution 4 from the separator 104 downstream of the second demetalling step (c). The product 12 from contactor 101 is directed to separator 102, for performing the first separation step (b) wherein the aqueous solution 2 comprising the salt of the cobalt carbonyl anion is separated from the organic reaction product 13 having a reduced cobalt metal content. An offgas stream 21 may also be separated in separator 102. The recycling step (d) according to the invention is performed by recycling aqueous solution 2 to the hydroformylation reaction 200, optionally after concentrating at least part of the solution 2 by removing water therefrom.

The reaction product having reduced cobalt metal content 13 is directed to the contactor 103, where the second demetalling step (c) is performed by contacting the stream 13 with an aquous solution 3 of an acid, which may advantageously be based on the free water 5 available from separator 100. If needed, make-up water 8 may be added. Free water 5 may already contain formic acid for performing the second demetalling step (c), but further make-up formic acid 6 may be added to contactor 103. An oxidant 7, such as air or a hydrogen peroxide solution, may also be added to contactor 103. In contactor 103, essentially all the cobalt present is converted to $Co^{2+}$, mostly present as cobalt formate and dissolved in the water phase. The product 14 from contactor 103 is directed to separator 104, for performing the second separation step (e) wherein the aqueous solution 4, primarily of cobalt formate, is separated from the cobalt-depleted organic reaction product 15, preferably with the help of a coalescer. An offgas stream 22 may also be separated in separator 104. The offgas streams 20 and 21, and optionally also 22, are directed to offgas scrubber 105, where they are contacted with preferably a part of the cobalt-depleted organic reaction product 15 or alternatively a part of the aqueous cobalt formate solution 4 separated in separator 104, used as first absorption liquid 25 to absorb any volatile cobalt carbonyl from the gas into the liquid phase. The cobalt-containing first absorption liquid 26 from scrubber 105 is directed to second demetalling step (c) in contactor 103. Offgas 23 essentially does not contain any more cobalt and is removed for further use, such as fuel. Cobalt make-up 9, preferably in the form of cobalt acetate, is added to the aqueous cobalt formate solution 4 that is directed from separator 104 to the contactor 101 as aqueous solution 1.

The techniques of the present invention may be used in the cobalt catalysed hydroformylation reactions as described in WO 2005/058787. The products of such a cobalt catalysed reaction include aldehydes, alcohols, formate esters, acetals, ethers, ether-alcohols, as well as unreacted olefins and paraffins. The cobalt-depleted organic reaction product 15 can be hydrogenated to produce high purity alcohols. A preferred hydrogenation reaction is described in WO 2005/058782. Alternatively the aldehydes may be optionally purified and oxidised to produce an acid, using conventional oxidation techniques. The high purity alcohols may then be used for example in the production of plasticiser esters and synthetic lubricants. Preferred esterification reactions are described in WO 2005/021482 and in our co-pending patent applications PCT/EP2008/001837 and PCT/EP2008/001838, which published as WO 2008/110305 and WO 2008/110306 respectively. Also the acids may be esterified with an alcohol to form an ester. If this alcohol is a polyol, a polyol ester is typically produced. Optionally, not all of the hydroxyl functions of all polyols present are esterified, and free alcohol functions may remain present in the polyol ester, such as from 5 to 35% relative to the starting alcohol functions in the polyol. These polyol esters may also find use as synthetic lubricants. Further esters of commercial interest may be made by esterification of the high purity alcohols produced according to the invention, with an acid or anhydride. The acid or anhydride preferably is selected from the group consisting of adipic acid, benzoic acid, cyclohexanoic acid, phthalic acid, cyclohexanoic dicarboxylic acid, trimellitic acid, or any of their anhydrides, or mixtures thereof.

In a further embodiment, the aldehyde containing materials may be purified to isolate the aldehydes, and these may be oxidised to produce carboxylic acids, which may be used in the production of synthetic esters, which in their turn may be used as lubricants. Alternatively, the acids may be used in the production of metal salts, which find use as additives in a wide range of applications.

In an embodiment, the invention therefore provides a process further comprising hydrogenating the cobalt-depleted organic reaction product and recovering an alcohol product from the hydrogenation product. The alcohol product may contain from 5 to 13 carbon atoms, such as from 7 to 11 or from 8 to 10, such as 9 carbon atoms. The alcohol product may be an alcohol mixture, and this mixture may have an average carbon number of from 5 to 13 carbon atoms, such as having an average carbon number between 8 and 13, such as between 8.5 and 10.5 or between 8.5 and 9.5.

In another embodiment, the invention provides for a process further comprising the esterification of the alcohol product or product mixture with an acid or anhydride to form an ester. The acid or anhydride is preferably selected from the group consisting of benzoic acid, phthalic acid, adipic acid, trimellitic acid, cyclohexanoic acid, cyclohexanoic dibasic acid, pyromellitic acid and their anhydrides. Particularly the phthalate esters, typically produce from phthalic anhydride, are of significant commercial importance.

The ester molecules produced using the process of the invention may comprise aromatic rings, such as alkyl benzoates, di-alkyl phthalates or tri-alkyl trimellitates. The aromatic rings in these ester molecules may be hydrogenated to produce the corresponding cyclohexanoic equivalents, such as mono-alkyl, di-alkyl or tri-alkyl cyclohexanoates. In particular, DINP may be further hydrogenated to form di-isononyl cyclohexanoate. The process of the invention may therefore be for the production of a phthalate di-ester, in particular DINP, and further comprise the hydrogenation of the phthalate di-ester to the corresponding cyclohexanoate, in particular di-isononyl cyclohexanoate.

Suitable hydrogenation processes to produce such cyclohexanoates, and catalysts for these processes, are disclosed in EP 5737, EP 1042273, EP 814098, EP 1412082, EP 1899051 or its equivalent CA 2612435, EP 1511582, EP 1549603, US 2004/0260113, US 2006/0149097, US 2006/0166809 and WO 2004/046078. We prefer to use a supported active metal catalyst, preferably having Ru as at least one of the active metals, and more preferably comprising ruthenium on a silica or on a carbon support.

The metal loading may be in the range of 0.1 to 10% by weight, based on the total weight of the catalyst. A higher catalyst activity allows operating the process at a lower temperature, at which side reactions are better suppressed, and thus a higher selectivity to the desired product may be achieved. Typically the catalyst activity is proportional to the metal loading. On the other hand, many active metals are rather precious and costly, making catalysts with higher metal loadings more expensive. Higher metal loadings may also lead to more metal clustering, thereby loosing some of the gains of the higher metal loadings. We therefore prefer to use active metal loadings of at most 5% by weight, more preferably at most 2% or even 1% by weight, and more preferably around 0.5% by weight, in particular when Ru is the prime or the only active metal present. Our preferred catalyst contains 0.5% by weight of ruthenium, alone or in the presence of other metals.

Also for activity reasons, we prefer to have the active metal well dispersed, such as a catalyst with a metal dispersion of 60-80%, meaning that the average active metal particle size is at most 5.0 nanometer (nm) or 50 Angstrom, preferably at most 3.0 nm, more preferably at most 2.0 nm and most preferably in the range of 1.0 to 2.0 nm (i.e. 10-20 Angstrom). Preferably we have good nanoscale homogeneity of the active metal, meaning no clustering of the Ru or other metal on a nanometer or transmission electron microscopy (TEM) scale, with little to no islands of metal clusters. For this purpose, we prefer that the average distance between the metal particles is larger than 2 times the average diameter of the particles, more preferably larger than 4 times the average diameter. We prefer to use metal precursors other than metal chlorides, such as nitrates, but more preferably organic precursors, such as acetates, succinates or amines, even more preferably the precursors described in WO 2004045767, because this reduces the risk of having residual chloride on the catalyst, and also tends to lead to smaller metal particles and a better metal distribution.

We also expect that by providing a small amount of a second metal, such as 5-10% by weight and based on the total weight of active metal, preferably of platinum, and preferably introduced by co-impregnation with the active metal, the stability of the catalyst activity may be improved, most probably because it reduces the tendency of the metal particles for clustering.

We prefer to use so-called coated catalyst, i.e. catalysts that have the active metal or metals located towards the outside of the catalyst particles, such as described in U.S. Pat. No. 5,600,031 and CA 2,612,435, e.g. with all or at least 80% of the active metal, based on the total amount of active metal, in an eggshell-type zone in the catalyst particles from the outer surface up to a penetration depth of at most 200 micrometer (μm), more preferably at most 150 μm, even more preferably at most 100 μm and yet more preferably at most 50 μm.

As support for the catalyst, we prefer to use a support that provides an average pore diameter of at least 3 nm (30 Angstrom), preferably at least 4 nm and more preferably at least 5 nm. We like to use extrudates as catalyst particles, but spheres would also be suitable. We prefer to use extrudates having a quadrilobe shape. The support for this catalyst preferably has large pore dimensions, but this comes at the expense of particle crushing strength and surface area. The average nominal diameter of our extrudates may be as high as 3 mm, and is preferably at least 1 mm, more preferably at least 1.3 mm, even more preferably at least 2 mm and yet more preferably at least 2.5 mm. As a further improvement, we prefer to use a support having a pore size distribution which is bimodal. In a preferred embodiment, the pore size distribution of the support has at least one first peak and at least 50% of the pore volume in the mesopore range with a pore diameters from 2 to 50 nm, and at least one second peak and at most 50% of the pore volume in the macropore range with pore diameters from 50 nm to 10000 nm. The average side crushing strength of our catalyst extrudates is preferably at least 10 N/mm, more preferably at least 12 N/mm with no more than 10% of the particles having less than 8 N/mm. Even more preferably the average side crushing strength of the extrudates is above 17.8 N/mm (4 lb force/mm) and yet more preferably above 22 N/mm (5 lb force/mm). When we use silica in or as the support, we preferably use amorphous silica, or a structured material such as MCM-41. If we select to have activated carbon in or as the support, we prefer to use carbon of which the surface has little to no residual acid sites present, and which has a surface area, measured according to the BET method, in the range of 100-1000 $m^2/g$, preferably at least 200, more preferably at least 500, even more preferably at least 800 and typically around 900 $m^2/g$. For obtaining the better crush strengths, we prefer to use peat carbon, more preferably coconut carbon for the support. The preferred supports provide a higher selectivity to the desired cyclohexanoate, and cause lower formation of byproducts, especially light byproducts. This simplifies the hydrogenation process, as less product cleanup is required in order to produce a high quality cyclohexanoate. This benefit is particularly important when the cyclohexanoate product needs to be low in remaining aromatic ring content, such as low in phthalate content, e.g. less than 100 ppm by weight of phthalate content, which requires the hydrogenation process to achieve a very high conversion. We prefer to produce the catalyst according to the method giving the smaller and more homogeneous distributed metal particles, which is described in "Supported Metal Catalysts: Some Interesting New Leads In An Old Field" by Stuart L. Soled et al, published in Studies in Surface Science and Catalysis (2006), 162 (Scientific Bases for the Preparation of Heterogeneous Catalysts), pages 103-110, Elsevier B.V., CODEN: SSCTDM and ISSN: 0167-2991. More details are disclosed in WO 2004045767. We have found that this improved metal distribution, e.g. on a 0.5% Ru on Silica support, provides a higher catalytic activity and a better maintenance of the activity over time, as compared with traditionally impregnated catalysts having the same metal loading and support, as it minimizes metal coalescence.

We have also found that these supported metal catalysts, in particular those which contain palladium as the main active metal on a carbon support, are particularly suitable for preforming or the carbonylation of cobalt (II) salts into cobalt carbonyls, a process step that is part of many hydroformylation processes, such as the processes that are disclosed in U.S. Pat. No. 5,600,031, in our copending patent application U.S. Ser. No. 61/092,835, and in this document including the background section.

In yet another embodiment, the invention therefore provides a process wherein the ester is a phthalate and further comprising the hydrogenation of the phthalate ester to a hexahydrophthalate ester.

The olefinic material that is hydroformylated may comprise short or long chained compounds containing olefinic unsaturation, depending on the final product desired. Most organic compounds possessing at least one non-aromatic carbon-carbon double bond may be reacted by this method. Generally the compound will have at least three carbon atoms although hydroformylation using ethylene is known (see, for instance, U.S. Pat. No. 6,150,322). Thus, straight and branched-chain olefins such as propylene, butylenes, pentenes, hexenes, heptenes, octenes, nonenes, decenes, undecenes, dodecenes, tridecenes and tetradecenes, styrene, olefin oligomers such as di- and tri-isobutylene and hexene and heptene dimers, olefinic fractions from the hydrocarbon synthesis process, thermal or catalytic cracking operations, and other sources of hydrocarbon fractions containing olefins, and mixtures of all of these, may be used as starting material, depending upon the nature of the final product desired. The feed may include a mixture of isomers, both skeletal and in double bond location or it may be isomerically pure (or nearly so), skeletally and/or in terms of double bond location.

In a preferred embodiment, the olefinic material is a mixture of olefins having a carbon number of from $C_3$ to $C_{18}$, more preferably $C_5$ to $C_{18}$. It will be recognized that the olefin feed may not consist of 100% olefins, nor of 100% olefins within the specified carbon number range, but may be a distribution of olefins having different carbon chain lengths. In a particularly preferred version of this embodiment at least 50% wt, preferably 70% wt, more preferably 80% wt, still more preferably 90% wt of olefins are in the specified carbon number range. In certain cases it may be preferable to use a feed of 100% wt (or nearly so) of the specified carbon number or carbon number range.

In another preferred embodiment, the olefinic material is the olefinic reaction product of the acid catalyzed oligomerisation of propylene and/or butenes, which may also optionally also include pentenes. Ethylene may be present in minor quantities, as well as trace quantities of dienes or acetylenes such as butadiene, methyl acetylene, and propadiene. Heavier olefins may be added to the feed, preferably selectively separated and recycled from the oligomerisation product, to selectively increase the production of selected carbon number products.

In yet another preferred embodiment, the olefinic material is the olefinic reaction product of the oligomerisation of various lower olefins and compounds having olefinic unsaturation, using regular or surface deactivated zeolite catalysts such as those described in U.S. Pat. Nos. 3,960,978; 4,021,502; 4,076,842; 4,150,062; 4,211,640; 4,520,221; 4,522,929; 4,524,232; 4,547,613; 4,568,786; 4,855,527; 4,870,038; 5,026,933; 5,112,519; 5,245,072; 5,417,869; 5,985,804; and 6,013,851.

Even more preferred as olefinic material in the present invention are $C_6$ to $C_{26}$ olefins, such as $C_8$ to $C_{26}$ olefins, more preferably $C_8$ to $C_{23}$ olefins, most preferably $C_8$ to $C_{18}$ olefins, conveniently prepared by contacting lower olefins under polymerization conditions with multidimensional acidic zeolites such as H-ZSM-57, or with siliceous one-dimensional acidic zeolites such as ZSM-22 and ZSM-23 zeolite having pore activity, wherein the zeolite surface may be rendered substantially inactive for acidic reactions.

By "lower olefins" or "lower olefinic material" as used herein is simply meant that the starting material to be oligomerised over the zeolite has lower carbon numbers than the final product. The oligomers may be dimers, trimers, tetramers or higher oligomers, or mixtures thereof. It is preferred that the starting material is a $C_3$ or greater olefin (or mixtures thereof), and in a preferred embodiment the olefinic material supplied to the oxonation reactor(s) according to the present invention is derived from the oligomerisation of $C_3$ and/or $C_4$ olefins using the aforementioned modified zeolites. In a particularly preferred embodiment, a feed is used comprising butenes (more preferably n-butene) and propylene in the ratio of about 1:0.01 to 1:0.049% wt. Conveniently, paraffins are also present in the feed to act as a heat sink in the reaction. The amount of paraffins to use to provide a desired heat sink function can be readily determined by one of ordinary skill in the art.

In another embodiment the process of the invention uses LAOs and/or LIOs (linear alpha olefins and linear internal olefins, respectively), which terms are well-known in the art, as olefinic material.

Other olefinic materials that may be used as a feed into the oxonation or hydroformylation reactors include oligomers produced by the Octol® process or the Dimersol® process. See, for instance, the previously mentioned U.S. Pat. No. 6,015,928. Octol® and Dimersol® are registered trademarks owned respectively by Degussa and Institut Français du Pétrole (IFP). Other preferred olefinic materials may be made using the process as described in U.S. Pat. No. 6,437,170. Yet other olefinic materials include oligomers produced using solid phosphoric acid (SPA) catalysts and those produced using ZSM-5, ZSM-57 and/or SAPO-11 catalysts, procedures which are known in the art. Other olefinic materials may be produced using oligomerisation processes as disclosed in WO 2006/133908, WO 2006/133967 or WO 2007/006398.

An alternative feed to the hydroformylation process, but even more preferred as feed to any of the oligomerisation processes mentioned, comprises 0.1-20% wt. isoolefin, particularly isobutylene and/or isoamylene, more preferably wherein the content of the isobutylene and/or isoamylene is from 0.5-5.0% wt. A preferred source of such a feed is the unreacted effluent from a methyl tertiary butyl ether (MTBE) unit. Another preferred source is the heavier byproduct stream of an oxygenate-to-olefins process, which may be rich in C4 and C5 olefins, up to 85 or 90% wt $C_4$+$C_5$, and typically only being 1-5% branched, but may in addition also contain some $C_3$ and possibly also some $C_6$ compounds, again mainly olefinic.

Typical hydroformylation reaction conditions include a temperature of about 125° C. to about 200° C. and/or a pressure of about 100 bar to about 350 bar, and/or a catalyst to olefin ratio of about 1:10000 to about 1:1. The molar ratio of hydrogen to carbon monoxide is conveniently in the range of about 1 to about 10. The process may also be carried out in the presence of an inert solvent such as a ketone, e.g., acetone, or an aromatic compound such as benzene, toluene or xylenes.

Any type of hydroformylation reactor may be operated in combination with the present invention, although those reactors are preferred that are more tolerant to the presence of a free water phase. Suitable hydroformylation reaction systems are described e.g. in U.S. Pat. No. 3,830,846, U.S. Pat. No. 6,444,856, U.S. Pat. No. 6,642,420, U.S. Pat. No. 6,723,884, U.S. Pat. No. 4,320,237, U.S. Pat. No. 6,720,457 and U.S. Pat. No. 6,015,928. A particularly suitable hydroformylation reactor is described in WO 2008/051301, more preferably as back-end reactor downstream of one or more loop reactors in a series reactor setup.

We have also found that pressure control is important in operating a hydroformylation reaction. We have found it advantageous to control the syngas supply pressure to the hydroformylation reactor by controlling the inlet pressure to the high pressure (HP) compressors. This allows the reactor pressure to be kept as high as possible. We have found that this control is preferably done by controlling a recycle flow of intermediate pressure (IP) offgas from downstream to the HP compressor. This IP offgas is separated from hydroformylation reactor product, optionally but preferentially after cooling the reactor product, separating excess gas from the reactor outlet in a high pressure separator, and letting the liquid from this separator down to a lower pressure. This pressure let down may also be done in a plurality of steps, and each step may then result in an IP offgas, usually at different pressures. These offgasses will have different compositions, due to differences in vapour/liquid equilibriums for the individual stream components. Depending on their composition, there may be preferences for purging one or a selection of those streams, possibly only in part, and preferably recycling more of the other offgas stream or streams. In many cases it is more desirable to purge IP offgasses than HP offgasses, to control the build-up of inerts in the gas system around hydroformylation. This is particularly true for control of inerts such as methane and carbon dioxide, but may be less desirable to control nitrogen. Suitable purge and recycle schemes are also disclosed in WO 2005/058787.

The crude aldehyde product of the invention, optionally after washing in a counter-current water wash tower for removing traces of catalyst and remaining acid from the demetalling step, but preferably without such a washing step, is typically hydrogenated to produce a so-called hydro product. Typically such hydrogenation employs a heterogeneous catalyst and many types of catalysts are suitable. Upstream of the hydrogenation catalyst, we prefer to provide an additional adsorption step to remove the last traces of cobalt that may be left over in the hydroformylation product. More details may be found in US 2006/0129004. Passing the hydrogenation feed over an adsorbent, such as a bed of pumice or spent catalyst or any other suitable solid support, preferably already at hydrogenation reaction conditions and in the presence of hydrogen, we have found is most effective in protecting the hydrogenation catalyst from cobalt deposits. WO 2005/058782 discloses suitable hydrogenation catalysts and processes, as well as conditions that are suitable for operating the pumice filters. In addition, we have found a sulphided cobalt/molybdenum catalyst to be particularly suitable in this service. Also particularly suitable are the reduced nickel-molybdenum catalysts, e.g. carried on alumina support, that are disclosed in X. Wang et al, "Characterization of Active Sites over Reduced Ni—Mo/$Al_2O_3$ Catalysts for Hydrogenation of Linear Aldehydes", J. Phys. Chem. B 2005, 109, 1882-1890, which catalysts we have found are also suitable for hydrogenation for branched aldehydes. These catalysts preferably contain no, or only small amounts of phosphorus, such as 0-1.0% wt. P, more preferably 0-0.5% wt. P, as disclosed in U.S. Pat. No. 5,382,715. Most preferably they are substantially free of phosphorus, as disclosed in U.S. Pat. No. 5,399,793.

For more details about suitable hydrogenation reactors and their internals, we refer to co-pending application PCT/EP2008/053783, which published as WO 2008/128852. We prefer to use a partial recycle of hydrogenation product over the hydrogenation reaction in order to dilute the aldehyde concentration and reduce the temperature increase. This may be achieved by hydrogenation product recycle or by inter-reactor recycle when multiple reactors are used in series.

The hydrogenation reaction converts aldehydes, acetals, formate esters and acids into alcohols. The reaction typically takes place at 160-200° C. and at a hydrogen partial pressure of at least 30 bar, preferably at least 50 bar, and more preferably in the range of 70-100 bar. Generally the conditions in the hydrogenation section are such that traces of aldehydes and formate esters are left behind in the hydrogenation product. These traces may be distilled from the product alcohol in the distillation section that separates the product alcohol from the hydrogenation product. Such a distillation unit typically comprises distillation towers lined up in a 2-tower heart cut formation where the product alcohol is taken as overhead of the second tower. However, this is not preferred because of the loss of some of the product alcohol in the byproduct streams that is typically associated with such distillation operation. We therefore prefer to provide an extra so-called hydrofinishing step on the distilled alcohol stream, to convert also most of the remaining traces of aldehydes and formate esters in this stream. Another option is to include a treatment with $NaBH_4$, and this may be performed before distillation on the hydrogenation product, but preferably on the distilled alcohol stream.

Many hydrogenation catalysts are suitable for hydrofinishing service, and we prefer a nickel catalyst because of its high activity and selectivity at mild conditions. If the catalyst employed in the upstream hydrogenation is tolerant to sulphur, such as a sulphided catalyst described above, we prefer to also use a sulphur tolerant catalyst in hydrofinishing service.

The operating conditions in hydrofinishing are preferably a compromise between the promotion of the desired reactions that convert the aldehydes and formate esters, and the limitation or suppression of the side reactions producing lights and/or heavies, such as alcohol dehydration to olefins, possibly followed by olefin hydrogenation to paraffin, etherification of alcohols to di-alkyl ethers, esterification of trace acids with alcohols to di-alkyl esters plus water, etc. The hydrofinishing conditions are usually such that any lights and/or heavies made in hydrofinishing do not need to be removed from the product alcohol. Optionally an additional drying step may be provided to bring the water content down, such as below the typical spec of 500 ppm wt. For safety reasons, dissolved hydrogen remaining after hydrofinishing or from the $NaBH_4$ treatment is preferably removed before sending the product alcohol to storage. This may be achieved by any suitable means, but we prefer to strip the product alcohol with a nitrogen stream, preferably a dry nitrogen stream, such that this stripping acts as a drying step because at the same time also the water content of the product alcohol is reduced.

We have now found that the upstream hydrogenation step may be performed in such a way that the need for the downstream hydrofinishing step is reduced and even eliminated. The hydrogenation reaction section typically comprises a plurality of reactors containing catalysts of different age and thus of different activity. We have found that when the average activity of the catalysts and the residence time in hydrogenation are sufficiently high, the extra hydrofinishing step may be dispensed with. For a Ni/Mo catalyst, we have found that an average activity of at least 9 h$^{-1}$ at the reference temperature of 170° C., combined with a superficial residence time of at least 0.6 h are sufficient. We prefer at the same time to keep the hydrogenation reaction temperatures in the range from 150 and 200° C. We also prefer at the same time to provide from 2 to 3% wt of water in the hydrogenation reaction, relative to the liquid hydrogenation feed. This water addition may be split over several reactors. At the same time, we prefer to keep the acid number of the hydrogenation reaction product below 3 mg KOH/g, more preferably at most 2 mg KOH/g, even more preferably at most 0.5 mg KOH/g. With aldehyde-rich hydrogenation feeds, we also prefer to recycle part of the hydrogenation reaction product, or an intermediate stream taken from an intermediate point between two or more reactors in series, to the hydrogenation feed. We prefer to recycle sufficient material to dilute the aldehyde content in the feed to the hydrogenation lead reactor down to a level in the range of 10-20% wt. This recycle helps in controlling the lead reactor exotherm, such as in the range from 10 to 30° C., while at the same time keeping the lead reactor inlet temperature high, such as at least 150° C., 160° C. or 170° C., while the highest reactor outlet temperature, typically of the lead reactor, may be kept at 200° C. or below. We have found that these conditions represent a desirable temperature profile, providing sufficiently high catalyst activity to avoid excessive reactor volume, while avoiding excessively high temperatures at which lights and heavies are formed. These preferred conditions may be different but may readily be determined by the skilled person for the other catalysts described here or in WO 2005/058782, in particular for copper chromite catalyst, or a combination thereof with Ni/Mo. We have found that the described hydrogenation operation may eliminate the need for providing a hydrofinishing step, or allow that such a hydrofinishing step is bypassed and shut down for at least a part of the hydrogenation reaction run during which the average catalyst activity is sufficient.

We have found that there are advantages to bringing preformed cobalt to the hydroformylation reactors, as compared to bringing Co$^{2+}$ to the hydroformylation reactors and preforming this into Co$^{-1}$ in those reactors. The processes bringing preformed cobalt to the hydroformylation reactors, such as the process according to the present invention, are particularly tolerant to feeds containing dienes, more particularly conjugated dienes. We have found that these processes are able to process feeds with significant amounts of dienes, even conjugated dienes. We have found that such processes are able to process feeds containing dienes at concentrations up to 5% wt, such as C$_5$ raffinate streams from isoprene extraction units, of which the typical olefin content is around 50% wt, and diene levels may be as high as 3 or even 3.5% wt. On higher molecular weight streams, this acceptable diene level is even higher. We have found that those processes, wherein the cobalt catalyst needs to be converted to its active carbonyl form in the presence of its olefin feedstock, are impaired when dienes are present in the feedstock. This is because the dienes, particularly conjugated dienes, appear to significantly reduce the so-called cobalt preforming reaction, wherein cobalt is converted from its starting compound, such as cobalt oxide or cobalt salt such as formate, acetate, or an oil soluble salt such as e.g. oleate, to its active carbonyl form, a reaction that is believed to be autocatalytic and thus impaired if the resulting carbonyl form is being tied up by e.g. a diene.

Many of the steps of the processes disclosed herein may consume hydrogen, in particular the hydroformylation step, any hydrogenation step, and the hydrofinishing step, if present. Also the hydroformylation may be fed additional hydrogen for gas composition control, such as explained in WO 2005/058787. The hydrogen may be supplied from a variety of sources, such as but not limited to refinery processes, partial oxidation (POX) of various starting materials, steam reforming, autothermal reforming (ATR) or the like. One of the potential sources of hydrogen is a refinery process called catalytic reforming, sometimes also called a Platforming process, wherein a refinery liquid stream, typically a naphtha or equivalent containing primarily naphthenes and/or paraffins in the C6 to C11 range, is converted to a product rich in aromatics over a heterogeneous precious metal chloride catalyst. These kind of processes are often known as a "Powerformer" or "Powerforming" processes (developed by Exxon), or as Continuous Catalyst Regeneration (CCR) processes (as e.g. offered by UOP and IFP). The hydrogen from such catalytic reforming processes contains small amounts of chloride, at a level in the order of 1-10 ppm by volume. It is believed that most of this chloride is present as hydrogen chloride, which is more readily detected by direct gas analysis and at a typical level of 4-8 ppmv. It is however suspected that, in addition, also organic chlorides may be present, and possibly even at similar levels as the HCl. Many hydrogen consuming processes are sensitive to chloride poisoning, and a chloride removal step is typically foreseen to remove HCl from the catalytic reforming hydrogen byproduct, most typically down to a level of at most 1 ppmv. A typical chloride removal step is the adsorption of chloride over activated alumina, such as alumina 9139A from UOP, Cl-750 and Cl-760 from BASF, Alcoa 760 from Alcoa, Puraspec from Johnson Matthey, over ZnO such as members of the Süd-Chemie Actisorb Cl series, e.g. Cl 13, and/or over a molecular sieve, such as type CLR-454 obtainable from UOP or Unimol types from Unicat.

Some of the typical process steps in the production of the oxygenates, such as the alcohols, disclosed herein, may however be particularly sensitive to chloride poisoning, such as a copper chromite hydrogenation catalyst used for aldehyde hydrogenation. The alcohol production process may also employ a hydroformylation catalyst cycle comprising a closed loop with minimal purge, in particular an aqueous closed loop, such as with several of the techniques discussed herein and/or disclosed in our co-pending patent application U.S. Ser. No. 61/092,835. Organic chlorides may become again converted to HCl in these processes. The traces of chloride coming with the hydrogen from a source such as a catalytic reforming may therefore build up in any of these aqueous loops to levels where corrosion due to chloride may become problematic, and/or where the chloride acts as a poison to the chemistry of the hydroformylation catalyst cycle, such as in a preforming step. The hydrogen from the catalytic reforming unit as feed to the alcohol production process therefore may need to be cleaned up to a lower level of chloride than for other hydrogen consuming processes, preferably to a level of at most 0.1 ppmv and more preferably at most 0.02 ppmv of chloride. We have found that the catalytic reforming hydrogen may also contain organic chloride compounds, at a concentration up to 10 ppm volume. Further we have found that organic chloride compounds are more difficult to remove by adsorption on the conventional adsorbents. Organic chlorides may therefore more easily pass through the adsorbent bed and still may cause problems in the alcohol production process. In addition, an activated alumina adsorbent may also convert part of the HCl in the hydrogen to organic chloride compounds. The activated alumina may react with HCl to form $AlCl_3$. This $AlCl_3$ is a catalyst for the formation of organic chlorides, and also for polymerising trace olefins in the hydrogen stream to form heavier components, sometimes referred to as "green oil". Organic chlorides are more difficult to detect, and typically do not show on the conventional chloride analytical methods, such as the well known Dräger tube.

We have found that an alkali treated molecular sieve, more particularly an alkali treated zeolite, is less prone to producing organic chlorides and performs much better in such chloride removal service, also adsorbing organic chloride compounds, while capable of reaching chloride loadings of up to about 20-22% wt on the adsorbent, expressed on a dry and chloride-free basis. We prefer to use a chloride adsorbent based on an alkali-treated zeolite, more particularly a zeolite, having a pH of at least 10, preferably 11, when measured in slurry. The adsorbent may comprise other components such as magnesium aluminosilicate, and binder material, and may be in the form of spheres or extrudates. An example of a suitable alkaline zeolite is product NB 316 from CLS Industrial Purification, containing from 70-90% wt of zeolite and sodium oxide and from 10-30% magnesium aluminosilicate and having a body centre cubic crystal structure, a pH of 11, a nominal pore size of 10 Angstroms, and a surface area of 630 m2/g. The product is available as 1.6 mm diameter (1/16") spheres or as 1.6 mm (1/16"), 3.2 mm (1/8") or 4.8 mm (3/16") diameter cylinders. The zeolite of the adsorbent may be of mineral origin, or may be synthetic. The zeolite may have one single crystal structure, or be a mixture of zeolites with different crystal structures. We prefer to use a mixture of faujasite, having larger 12-ring pores, and Linde Zeolite A, which as smaller 8-ring pores. The adsorbent preferably comprises a binder material in addition to the zeolite, but could be binderless. Clay is a suitable binder material, such as chlorite. The adsorbent may be formulated from fresh zeolite, or may be based on a waste byproduct from a different process using a suitable zeolite as catalyst or adsorbent material, preferably after regeneration such as by oxidative regeneration. We prefer to use an adsorbent having a large surface area, of at least 300 m²/g, preferably at least 400 m²/g, more preferably at least 450 m²/g, typically 488 m²/g. Higher surface areas are also suitable, such as 500 m²/g or 600 m²/g and above. The activity and capacity of the adsorbent is preferably increased by treatment with an alkali solution, typically containing NaOH, $Ca(OH)_2$, KOH or a mixture thereof.

We prefer that only the hydrogen supply to the more sensitive consumers is treated with the alkali treated molecular sieve, so that the amount of generated spent adsorbent can be minimised. The catalytic reforming hydrogen going to the less sensitive consumers may preferably undergo only the conventional cleanup. When an activated alumina adsorbent is used for this conventional cleanup, we prefer to withdraw the hydrogen for treatment with the alkali treated molecular sieve upstream of the activated alumina adsorbent, so that the amount of organic chlorides in the hydrogen to be treated with the alkali treated molecular sieve is minimised. What is described here for hydrogen from catalytic reforming processes, is equally applicable to hydrogen from other sources that may contain chlorides for instance because of chloride being present in at least one their feedstocks.

The invention is now further illustrated with the following examples.

Example 1

Three 1.9 liter (half a gallon) continuous stirred tank reactors (CSTR) from Autoclave Engineering were operated in continuous mode and in series. Each reactor has a useful liquid volume of 1 liter, set by the height of the overflow tubes. A permanent excess syngas of about 20% over the amount of gas required for the reaction was installed to drive a continuous liquid transfer from reactor to reactor. A high stirring rate of 2000 RPM was used in all reactors to assure that the free water present is uniformly distributed in the organic phase and does not settle out as a separate layer. Due to dissolved and dispersed gas in the liquid, the useful liquid volume in the reactors was estimated as being about 800 ml.

Heating was delivered by means of external heaters. Accurate temperature control was assured by means of internal cooling coils. During the test work the oxo reactors were controlled at a temperature in the range of 160° to 175° C. as indicated below. The oxo reactor pressure was controlled at 300 bar gauge by means of a pressure regulator in the syngas feed. The reaction product is cooled at pressure down to ambient temperature (about 20° C.) and routed to a high pressure separator (HP Sep) where the excess gas is separated from the liquids. The offgas rate from the high pressure separator was controlled by means of a pressure regulator in combination with a metering valve and a wet gas flow meter at the top of the high pressure separator. The fresh syngas to the first oxo reactor had a $H_2$/CO molar ratio of 1.5. The olefin feed was a mixture of branched octenes obtained by the dimerisation of raffinate-2 over a stacked bed of zeolite catalyst containing H-ZSM-22 followed by H-ZSM-57 in series. The octene feed was delivered cobalt free to the first oxo reactor at a controlled flow rate of about 1400 ml/h.

As catalyst, an aqueous cobalt solution having 3.0 wt % total cobalt contained in the form of cobalt formate and of $Co[Co(CO)_4]_2$, also called "CoCo-salt", was used. Of the 3.0% wt cobalt in solution, 1.2% wt was present as $Co^{-1}$, assumed all being in the carbonyl form, and the remaining 1.8 wt % was present as $Co^{2+}$. The solution also contained 2.8% wt total formic acid. This aqueous cobalt solution was pumped into the lead oxo reactor at a ratio of 12% wt relative to the fresh olefin feed. The amount of total cobalt present, based on olefin feed, was therefore around 4100 wt ppm.

Steady state was established with all the oxo reactors at the same temperature. Samples were taken from each reactor (R1, R2 and R3) and from the high pressure separator (Prod), and analysed by GC to determine conversion and selectivities. The Oxo performances were determined at different temperatures, and are given in Table 1. The olefin conversion was calculated in mol % and excluding any hydrogenation to paraffins (so-called "Ex Paraffin").

TABLE 1

| Run No. | 1 | | | 2 | | | | 3 | | | |
|---|---|---|---|---|---|---|---|---|---|---|---|
| Temperature (° C.) | 160 | 160 | 160 | 170 | 170 | 170 | | 175 | 175 | 175 | |
| Sample | R1 | R2 | R3 | R1 | R2 | R3 | Prod | R1 | R2 | R3 | Prod |
| GC-results (wt %) | 35.69 | 18.37 | 13.80 | 25.00 | 12.93 | 11.13 | 10.01 | 22.89 | 10.96 | 10.13 | 9.68 |
| Olefins + paraffins | | | | | | | | | | | |
| Aldehydes + alcohols + | 52.42 | 56.63 | 54.9 | 48.49 | 37.96 | 34.51 | 62.83 | 46.81 | 42.78 | 60.63 | 53.15 |

TABLE 1-continued

| Run No. | 1 | | | 2 | | | | 3 | | | |
|---|---|---|---|---|---|---|---|---|---|---|---|
| formate esters | | | | | | | | | | | |
| Ethers | 0.33 | 0.61 | 0.67 | 0.48 | 0.79 | 0.86 | 1.00 | 0.54 | 0.92 | 0.92 | 1.09 |
| Ether alcohols | 0.45 | 0.93 | 1.31 | 0.81 | 1.46 | 1.74 | 2.57 | 0.89 | 1.92 | 2.28 | 2.82 |
| Acetals | 10.25 | 21.04 | 26.25 | 23.08 | 43.04 | 47.78 | 22.36 | 26.27 | 40.30 | 24.02 | 31.46 |
| Other heavies | 1.03 | 2.42 | 3.07 | 2.15 | 3.81 | 3.99 | 1.23 | 2.59 | 3.11 | 2.01 | 1.81 |
| Olefin Conversion (mol %) | 58.57 | 77.68 | 83.00 | 70.19 | 84.02 | 86.17 | 87.52 | 72.54 | 86.39 | 87.35 | 87.9 |

The high conversions already obtained in R1, and also in R2, illustrate that the reaction is not significantly delayed by any catalyst initiation. This benefit is associated with the presence of part of the cobalt catalyst feed being already in the carbonyl form, i.e. in the anion of the $Co[Co(CO)_4]_2$. This carbonyl is readily available as catalyst for hydroformylation and for any preforming of $Co^{2+}$ to further cobalt carbonyls, and no appreciable induction time is therefore noticed.

Example 2

The distribution of cobalt under oxo reactor conditions was determined in Example 1 for the lead reactor R1 in run 3 at 175° C. Analysis of a sample taken from the water phase after stopping the stirring for a few minutes showed 10000 wtppm of cobalt, and of the organic phase separated from a mixed phase sample taken during stirred operation showed about 1400 wtppm of cobalt.

The oil/water mixture from the high pressure separator during Example 1 was let down into an Intermediate Pressure Separator (IP Sep) operating at a pressure of 6-7 barg for performing preliminary separation step (g). Excess gas in the IP Sep was also separated off, combined with the excess gas separated at high pressure, and contacted with a volume of olefin feed in an absorber to remove any volatile cobalt entrained with the offgasses. The volume of combined offgas was measured by a gas meter at the outlet of the absorber.

The organic and water phases from the IP Separator were analysed for cobalt content. Compared to the results measured for the lead reactor under reactor conditions, the cobalt in the water phase had dropped to about 6000-7000 wtppm and the cobalt in the organic phase had increased to 2000-2400 wtppm.

This example demonstrates that cooling of the hydroformylation reaction mixture (10) before separating the two liquid phases (5 and 11) increases the amount of cobalt present in the organic phase (11) and reduces the amount of cobalt present in the water phase (5). As a result, more cobalt carbonyl becomes available with the organic phase for extraction in the first demetalling step (a). The cobalt concentration in the water phase (5) from the IP Separator is reduced. As a result, it is more suitable for routing directly to the second demetalling step (c), thereby bypassing the first demetalling step (a). Even when this water phase (5) is used as the only source of water in the second demetalling step (c), the cobalt concentration of the aqueous solution (4) from this step (c) is sufficiently low to avoid precipitation of cobalt salt, especially as cobalt formate, if necessary by keeping the solution at an elevated temperature, such as at 80° C.

A second effect of the bypass is an increased concentration of cobalt in the water (2) from the first demetalling step (a), which is separated in step (b), making it more suitable for recycle to the hydroformylation reaction (200) in step (d).

The improved cobalt distribution between the IP Separator liquids (5 and 11) creates and widens an operating window in which the water streams in the cobalt removal steps can be routed in a closed loop, as shown in the preferred embodiment of FIG. 1, and this without the need for including an evaporator to control the water balance and/or the need to dispose of a waste water stream.

Example 3

An aqueous cobalt solution containing also cobalt carbonyls (as CoCo-salt) was produced by contacting an organic oxo product, in which an amount of $Co_2(CO)_8$ was dissolved, at 80° C. with a dilute aqueous cobalt foilate solution containing 1.1% wt $Co^{2+}$ and 3% wt free formic acid, using the "disproportionation" reaction (3). The resulting aqueous phase was separated and analysed. It contained a total of 3.40% wt cobalt, of which 1.63% wt was present as $Co^{-1}$ and 1.77% wt as $Co^{2+}$. The solution also contained 2.2% wt total formic acid. This solution remained stable upon storage at 20° C. under nitrogen over several weeks, without showing any precipitation, e.g. of cobalt formate, or loss of $Co^{-1}$ content, in spite of the solubility of cobalt formate (alone) in water being only 1.2% wt at 20° C., measured as % wt cobalt.

This example illustrates that, for the same temperature, much more cobalt can be successfully dissolved into a stable aqueous solution containing cobalt formate by having a portion of the cobalt present as the carbonyl anion, or as CoCo-salt.

Example 4

Octene hydroformylation was performed in two parallel batch experiments for which all operating conditions were identical except that in one experiment the cobalt was added as cobalt formate and in the other as CoCo salt. The temperature of the reaction autoclave (CSTR) was 175° C. and the pressure 300 barg. The syngas feed had a molar ratio of $H_2/CO$ of 1.5. An amount of water equivalent to 12% wt based on the amount of the octene feed was added, in which an amount of cobalt corresponding to 0.13-0.14% wt based on the octenes were dissolved. The stirring rate was 2500 RPM. The autoclave pressure was kept constant by supplying more syngas. The consumption of syngas was monitored over time, and with a GC analysis of the organic products after the test, the evolution of conversion over time was back-calculated. It is again expressed in mol % and "Ex Paraffin".

The conversion obtained as a function of reaction time is given in Table 2. The experiment with cobalt formate clearly shows a reaction delay of more than 5 minutes to allow the reaction to start. This is not the case with Coco salt. The overall rate of reaction is significantly faster with Coco salt.

TABLE 2

| Reaction time | Octene Conversion (mole %) | |
|---|---|---|
| (minutes) | Cobalt formate | CoCo-salt |
| 0 | 0.23 | 0.64 |
| 5 | 1.09 | 5.69 |
| 15 | 8.04 | 22.63 |
| 30 | 27.83 | 58.66 |
| 45 | 48.71 | 76.33 |
| 60 | 66.78 | 83.50 |
| 90 | 83.02 | 87.67 |
| 120 | 87.79 | 89.17 |
| 180 | 90.04 | 90.45 |

This example illustrates very clearly that the hydroformylation reaction using as catalyst an aqueous solution containing cobalt carbonyls is not significantly delayed by any catalyst initiation, unlike when a solution of only a cobalt salt such as cobalt formate is used. The carbonyls readily participate as catalyst in the hydroformylation reaction, and are also readily available for the preforming of any $Co^{2+}$ present in the reaction zone to further cobalt carbonyls. The induction time observed with using only $Co^{2+}$ catalyst feed is therefore practically eliminated.

Example 5

The extraction of cobalt carbonyls in the first demetalling step (a) was demonstrated in continuous mode by contacting the organic product (11) from the IP Separator (100) from Example 2 with an aqueous solution (1) of cobalt formate. The solution contained 1.5% wt cobalt as $Co^{2+}$ and 2.8% wt total formic acid, thus including about 0.5% wt of free formic acid, i.e. in excess to the amount of $Co^{2+}$ present. The amount of water used for the contacting was the same as the amount of water used for the catalyst feed to the lead oxo reactor in Example 1, thus respecting the water balance over all the steps in the preferred catalyst cycle embodiment. The extraction demetalling step (a) was performed in a plug flow spiral tube with 2 mm internal diameter and 20 meter length, having an outlet pressure of 2 barg and being kept at a temperature in the range of 90-105° C. The superficial residence time of the liquids in the extraction step was about 1 minute. About 75% of the cobalt in the organic product (11) from the IP Separator (100) was extracted into the water phase (2), leaving about 400-600 ppm of cobalt in the organic product (13) after extraction. No significant effect of temperature on the extraction step was observed in the small range tested.

This example demonstrates that the first demetalling step (a) can be performed with high volumetric efficiency, so that equipment size and inventory of organic material can be minimised.

Example 6

The extraction step of Example 5 was repeated for a range of concentrations of $Co^{2+}$ in the aqueous solution. In addition to the aqueous solution introduced for the extraction, a portion of the water phase (5) from the IP Separator (100) was also added to the extraction step (a), as indicated in percent of the amount that is separated. The amount of aqueous solution for the extraction was reduced accordingly in order to keep the total amount of water in the extraction step the same. The total cobalt concentration in the water phase (2) obtained from the extraction step was determined and compared with the total cobalt concentration of the catalyst feed to the lead reactor, as defined in Example 1. The different extraction conditions and their results are shown in Table 3.

TABLE 3

| Catalyst feed (wt % total Co) | IP Sep water to extraction (%) | Extraction water (% $Co^{2+}$) | Solution from extraction (wt % total Co) | Extraction Temperature (° C.) |
|---|---|---|---|---|
| 3.00% | 52% | 1.20% | 2.15% | 90 |
| 3.00% | 52% | 1.20% | 1.90% | 100 |
| 3.00% | 52% | 1.20% | 2.00% | 115 |
| 3.00% | 12% | 1.20% | 2.38% | 110 |
| 2.94% | 12% | 1.58% | 2.55% | 100 |
| 3.10% | 0% | 1.54% | 3.00% | 100 |

This example demonstrates the capability to produce an aqueous solution (2) from the extraction step (a) that has the same total cobalt concentration and amount of the catalyst feed to the lead reactor. As a result, the entire amount of CoCo-salt solution (2) obtained from the extraction step may be used as catalyst feed to the hydroformylation reaction, such that the amounts of water are also in balance and the need for a water separation step can be avoided. This preferred embodiment may be achieved with about 1.5% wt $Co^{2+}$ in the solution (1) used for extraction, and with the entire amount of water phase (5) from the IP Separator (100) bypassing the extraction step (a).

Example 7

The operation of Example 1 in combination with the IP Separator (100) operation of Example 2 and the extraction step (a) of Example 5 was started in continuous mode. The aqueous solution (2) from the extraction step was monitored until a total cobalt concentration was measured that was equal to this of the aqueous catalyst feed to the lead oxo reactor, a condition that was obtained after about 4 hours of operation. At that moment, the supply of catalyst feed to the oxo reactor was switched over to the aqueous solution (2) from the extraction step, thereby running the experiment in closed loop on the CoCo-salt solution, closing recycle step (d) of the invention. The operation was continued for another 6 hours, while the composition of the CoCo-salt solution (2) was monitored. The results are shown in Table 4.

TABLE 4

| CoCo salt solution composition | | | |
|---|---|---|---|
| Time in closed loop (Hours) | Total Co wtppm | Fraction $Co^{-1}$ (%) | Total formic acid (wt %) |
| 0 | 28986 | 41% | 2.8644 |
| 4 | 29540 | 35% | 3.0195 |
| 6 | 29234 | 36% | 2.9906 |

This example demonstrates that the hydroformylation step (200) and the catalyst cycle can be operated in closed loop, according to the preferred embodiment shown in FIG. 1, in a stable manner.

Samples taken from the organic product (14) from the extraction step (a) showed a light yellow appearance but turned brown when standing on the bench for about 10-20 minutes. This colour change illustrates that the cobalt in the organic product (14) from extraction is present primarily in the form of $HCo(CO)_4$, instead of as $Co_2(CO)_8$. This demonstrates that the performance of the extraction step, here performed as a single stage in co-current mode, is limited by the equilibrium distribution of $HCo(CO)_4$ between the two liquid phases. The equilibrium distribution under the conditions of 2 barg and 105° C. in the extractor was calculated as about 0.062 gmole total cobalt per liter of organic phase per gmole of $Co^{-1}$ per liter in the water phase. This equilibrium limitation for a single co-current stage may be overcome by operating the extraction step (a) in counter-current mode and with more stages. This is expected to further broaden the operating window of the catalyst cycle when operated in closed loop.

Example 8

The organic product (13) from extraction in Example 7, containing about 500 wtppm of cobalt, was in continuous mode combined with the water phase (5) separated from the IP separator (100) in Example 2, which contained about 7000 wtppm of cobalt. These streams were decobalted together by contacting with a 10% aqueous solution of hydrogen peroxide (7), at 60° C. and at a pressure of 1 barg, through a contactor (103) comprising a series of static mixers and in which the total liquid residence time was about 1 minute. The amount of $H_2O_2$ used was 270% of stoichiometry based on the total amount of cobalt contained in the organic (13) and the water (5) feed stream to the contactor (103). After phase separation (e), the water phase (4) contained about 1.46% wt of cobalt. More than 99.75% of the cobalt from the two feed streams was retrieved in the water phase (4) after separation. Most of the balance was retrieved in the small amount of water entrained with the organic phase (15).

This example demonstrates that the oxidative decobalting step (c) can be very effective with short residence times and thus with high volumetric efficiency. Operating the extraction step (a) in combination but separate from the oxidative demetalling step (c) allows both steps to be performed with very small residence times, such that equipment size and the inventory of organic material can be kept very small. A further advantage demonstrated is that both demetalling steps may be performed at pressures below 6 barg, so that only low pressure equipment is involved and investment costs may be kept to a minimum.

Example 9

A 5 hour continuous demonstration run was performed with the hydroformylation step performed as described in Example 1 and connected to a decobalting process comprising many of the features shown in FIG. 1. The octene feed rate was kept constant at 1017 g/h. The reaction product 10 was treated as described in Example 2 and led into an IP separator 100. The organic product 11 was contacted with a cobalt formate solution 1 in the extractor 101 as described in Example 5 and separated in separator 102. The water phase 2 from this separator was recycled entirely to the lead oxo reactor in the manner described in Example 7. The organic phase 13 from separator 102 was combined with the water phase 5 from IP separator 100 and contacted with an aqueous hydrogen peroxide solution 7 as described in Example 8 in contactor 103. The organic phase 15 and water phase 4 from contactor 103 were separated in separator 104 and collected. As compared to the flow diagram shown in FIG. 1, streams 8, 9, 21, 22 and 26 had a zero flow, rate, stream 4 was collected in a first inventory instead of recycled to extractor 101, stream 1 was taken from a second inventory, and absorber 105 was operated as a vessel filled with a volume of olefin feed.

Table 5 shows the flow rates used or measured, and the stream compositions as established or measured during the demonstration run. The streams are referred to by the corresponding number in FIG. 1. Also given is the amount and composition of the small amount of free water that was entrained with stream 15 but separated out later in a decantor having a residence time of about 1 hour. With the help of a suitable coalescer in separation step (e), this water and cobalt should be recoverable as part of stream 4.

TABLE 5

| Stream Number | Phase | Flow rate (g/h) | $Co^{-1}$ (g/h) | $Co^{2+}$ (g/h) | Total Co (g/h) | Cobalt (wt %) |
|---|---|---|---|---|---|---|
| 11 | Organic | 1228.8 | 2.96 | 0 | 2.96 | 0.241 |
| 5 | Water | 130.2 | 0.45 | 0.46 | 0.91 | 0.696 |
| 1 | Water | 127.0 | 0 | 1.91 | 1.91 | 1.50 |
| 13 | Organic | 1228.8 | 1.07 | 0 | 1.07 | 0.087 |
| 2 | Water | 130.2 | 1.17 | 2.73 | 3.90 | 2.907 |
| 3 | Water | 130.2 | 0.45 | 0.46 | 0.91 | 0.696 |
| 15 | Organic | 1229.0 | 0 | 0 | 0 | |
| 15 | Water | 0.61 | 0 | 0.01 | 0.01 | 1.48 |
| 4 | Water | 126.4 | 0 | 1.88 | 1.88 | |

During the 5 hour run, an amount of cobalt was collected in the absorber 105 that corresponds to an hourly rate of 0.06 grams of cobalt contained in the combined HP and IP offgasses.

This example demonstrates that a process according to the flow diagram shown in FIG. 1 is stable and operable in continuous mode. Provided that air is used instead of the aqueous $H_2O_2$ solution in contactor 103, the recycle loops can be successfully closed, thereby minimising the consumption of chemicals to drive the catalyst cycle and reducing the amount of waste streams from the process. The residence times in the two demetalling steps may also be kept very low.

Example 10

A continuous stream of organic octene hydroformylation product after a demetalling treatment using a 100% stoichiometric excess of $H_2O_2$, supplied as a 10% wt solution, and a separation of the resulting aqueous solution in a separator providing a residence time of 15 minutes at 35° C., and thus similar to stream 15 in example 9, was fed with a flow rate of about 1.78 liter per hour to a coalescer, for a period of several hours. The coalescer used in the test was a Small Flow Liquid/Liquid Coalescer of the vertical type AquaSep Plus obtained from Pall Corporation, adapted for the small feed flow rate. The adaptation consisted in covering the internal surface of the coalescer medium with a teflon insert having a circular opening of 1.0 cm diameter to allow liquid flow onto the medium, and in directing the incoming flow with an internal pipe into the circular opening. The coalescer medium was a hydrophobic polymer membrane having a thickness of about 3-4 mm. The residence time in the coalescer medium was therefore only about 0.5-0.6 seconds. The small free water particles, present as a mist in the organic feed, were found to be removed from the organic and a small amount of water collected during the test in the bottom of the coalescer. The coalescer feed stream and the organic coalescer product stream were analyzed for $Co^{2+}$ and for $Co^{-1}$ as follows. A carefully weighed sample of the organic stream is first washed with cold demineralised water and subsequently washed three times with a dilute nitric acid solution. The aqueous phase resulting from the first water washing is weighed and analyzed for cobalt content, and this amount of cobalt is assumed representing the amount of $Co^{2+}$ present in the starting sample. The aqueous phases resulting from the dilute nitric acid washes are collected, combined, weighed and also analyzed for cobalt content. This amount of cobalt is assumed to represent the amount of $Co^{-1}$ present in the starting sample. The amounts of cobalt were converted to concentrations using the weight of the starting sample. The results of the test are shown in Table 6.

TABLE 6

| Coalescer Stream | Total Co (ppm wt) | Of which Co-1 (ppm wt) |
|---|---|---|
| Inlet | 33.1 | 5.7 |
| Outlet | 1.2 | 0.8 |

This example demonstrates the high effectiveness of a coalescer for removing the small traces of free water in the organic product from hydroformylation, which, downstream of an oxidative demetalling step for removing the cobalt hydroformylation catalyst, typically contains the biggest portion of the cobalt that is left over in the product.

Having now fully described this invention, it will be appreciated by those skilled in the art that the invention can be performed within a wide range of parameters within what is claimed, without departing from the spirit and scope of the invention.

The invention claimed is:

1. A process for hydroformylating an olefin feed in the presence of a homogeneous catalyst to form an organic hydroformylation reaction product, the catalyst comprising a carbonyl compound of a first metal which is cobalt, which process comprises:
    (a) performing a first demetalling step (101) comprising contacting the organic cobalt catalyst-containing reaction product (11) with an aqueous solution (1) of a salt of a second metal and a first acid, the first acid having a pKa of at least 1.5 at 25° C., to form an aqueous solution (2) comprising a salt of the second metal having cobalt carbonyl as anion,
    (b) performing a first separation step (102) on the product of step (a) which comprises separating the aqueous solution (2) from the organic hydroformylation reaction product to form an organic reaction product having reduced cobalt content (13),
    (c) performing a second demetalling step (103) comprising contacting the organic reaction product (13) separated in step (b), in the presence of an oxygen-containing gas or an oxygen-donating compound (7), with an aqueous solution (3) of a second acid to form (i) an aqueous solution (4) comprising a cobalt salt of the second acid and (ii) a cobalt-depleted organic reaction product (15), and
    (d) recycling at least part of the aqueous solution (2) separated in step (b) to the hydroformylation reaction (200).

2. The process according to claim 1 further comprising:
    (e) performing a second separation step (104) comprising separating the aqueous solution (4) from the cobalt-depleted organic reaction product (15) produced in step (c).

3. The process according to claim 1 wherein the second acid is the same as the first acid and the second metal is cobalt, and further comprising:
    (f) recycling at least part of the aqueous solution (4) separated in step (e) as the aqueous solution (1) to the first demetalling step (a).

4. The process according to claim 1 wherein the first acid is formic acid.

5. The process according to claim 1 wherein the amount of aqueous solution (2) recycled in step (d) to the hydroformylation reaction (200) is at least 3% and at most 30% by weight based on the weight of the olefin feed to the hydroformylation reaction.

6. The process according to claim 1 which further comprises:
    (g) performing a preliminary separation step (100) prior to step (a) comprising separating free water (5) from the hydroformylation reaction product (10) to form the cobalt catalyst-containing reaction product (11) for the contacting in the first demetalling step (a), and
    (h) using at least part of the free water (5) separated in step (g) as water for the aqueous solution (3) of the second acid in second demetalling step (c).

7. The process according to claim 6 wherein the additional separation step (g) is performed under a partial pressure of carbon monoxide of at least 3 bar.

8. The process according to claim 1 which comprises separating at least one volatile cobalt carbonyl-containing offgas stream in any of the steps (a), (b), (c), (d), and, when present, (e) and (g) and which further comprises:
    (j) performing a first absorption step (105) comprising contacting at least part of at least one of said separated offgas streams with a first absorption liquid (25) for absorbing at least part of the volatile cobalt carbonyl present in said offgas stream, thereby forming a cobalt-containing first absorption liquid (26), and
    (k) adding the cobalt-containing first absorption liquid (26) to the first demetalling step (a), the first separation step (b) or the second demetalling step (c).

9. The process according to claim 8 wherein the first absorption liquid (25) is at least part of the aqueous solution (4) formed in step (c) and, if present, separated in step (e).

10. The process according to claim 1 wherein the first demetalling step (a) further comprises:
    (l) contacting the organic cobalt catalyst-containing reaction product (11) with a stripping vapour to form a cobalt carbonyl-containing stripping vapour, and
    (m) performing a second absorption step comprising contacting the cobalt carbonyl-containing stripping vapour with a second absorption liquid to form a cobalt-containing second absorption liquid, which is directed to the hydroformylation reaction,
    wherein the cobalt carbonyl-containing stripping vapour from step (l) is prior to the second absorption step (m) cooled and cobalt-containing organics are condensed out, at least part of said cobalt-containing organics being pumped to the hydroformylation reaction, and wherein optionally also water is condensed out, and at least part of said condensed water is also recycled to the hydroformylation reaction.

11. The process according to claim 1 wherein the second demetalling step (c) comprises at least one co-current contacting stage.

12. The process according to claim 1 further comprising hydrogenating the cobalt-depleted organic reaction product (15) and recovering an alcohol product or product mixture from the hydrogenation product.

13. The process according to claim 12 further comprising the esterification of the alcohol product or mixture with an acid or anhydride to form an ester.

14. The process according to claim 13 wherein the acid or anhydride is selected from the group consisting of benzoic acid, phthalic acid, adipic acid, trimellitic acid, cyclohexanoic acid, cyclohexanoic dibasic acid, pyromellitic acid and their anhydrides.

15. The process according to claim 14 wherein the ester is a phthalate and further comprising the hydrogenation of the phthalate ester to a hexahydrophthalate ester.

* * * * *

UNITED STATES PATENT AND TRADEMARK OFFICE
CERTIFICATE OF CORRECTION

PATENT NO.       : 8,541,627 B2
APPLICATION NO. : 13/001922
DATED            : September 24, 2013
INVENTOR(S)      : Van Driessche et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 176 days.

Signed and Sealed this
Fifteenth Day of September, 2015

Michelle K. Lee
*Director of the United States Patent and Trademark Office*